(12) United States Patent
Kudenov

(10) Patent No.: US 9,074,993 B2
(45) Date of Patent: Jul. 7, 2015

(54) WHITE LIGHT ACHROMATIC GRATING IMAGING POLARIMETER

(75) Inventor: Michael W. Kudenov, Tucson, AZ (US)

(73) Assignee: The Arizona Board of Regents on Behalf of the University of Arizona, Tucson, AZ (US)

(*) Notice: Subject to any disclaimer, the term of this patent is extended or adjusted under 35 U.S.C. 154(b) by 478 days.

(21) Appl. No.: 13/399,861

(22) Filed: Feb. 17, 2012

(65) Prior Publication Data

US 2013/0027713 A1     Jan. 31, 2013

Related U.S. Application Data

(63) Continuation-in-part of application No. 13/225,315, filed on Sep. 2, 2011.

(60) Provisional application No. 61/402,767, filed on Sep. 3, 2010, provisional application No. 61/463,488, filed on Feb. 17, 2011.

(51) Int. Cl.
*G01N 21/21* (2006.01)
*G01J 4/04* (2006.01)

(52) U.S. Cl.
CPC .. *G01N 21/21* (2013.01); *G01J 4/04* (2013.01)

(58) Field of Classification Search
CPC .................... G01J 2009/0129; G01B 2290/70; G01B 2290/30
USPC .................. 356/451, 453, 456, 521, 491, 495
See application file for complete search history.

(56) References Cited

U.S. PATENT DOCUMENTS

| 5,781,293 | A | 7/1998 | Padgett et al. |
|---|---|---|---|
| 6,674,532 | B2 | 1/2004 | VanDelden |
| 6,687,007 | B1 | 2/2004 | Meigs |
| 2003/0142318 | A1 | 7/2003 | Kuiseko |
| 2005/0237532 | A1 | 10/2005 | Beale et al. |
| 2006/0250616 | A1 | 11/2006 | Pettipiece et al. |
| 2008/0278675 | A1 | 11/2008 | Escuti et al. |
| 2010/0110363 | A1 | 5/2010 | Escuti et al. |
| 2010/0171952 | A1 | 7/2010 | DeFlores et al. |
| 2010/0225856 | A1 | 9/2010 | Escuti et al. |

OTHER PUBLICATIONS

Crawford et al., "Liquid-crystal diffraction gratings using polarization holography alignment techniques," J. Appl. Phys. 98:123102 (2005).
Escuti et al., "Simplified Spectropolarimetry Using Reactive Mesogen Polarization Gratings," Proc. SPIE 6302:630207, (2006).
Kudenov et al., "Prismatic Imaging Polarimeter Calibration for the Infrared Spectral Region," Opt. Exp. 16:13720-13737 (2008).

(Continued)

*Primary Examiner* — Hwa Lee
(74) *Attorney, Agent, or Firm* — Klarquist Sparkman, LLP

(57) ABSTRACT

White-light snapshot channeled linear imaging (CLI) polarimeters include polarization gratings (PGs) configured to produce a compensated shear between portions of an input light flux in first and second polarization states. The disclosed CLI polarimeters can measure a 2-dimensional distribution of linear Stokes polarization parameters by incorporating two identical PGs placed in series along an optical axis. In some examples, CLI polarimeters are configured to produce linear ($S_0$, $S_1$, and $S_2$) and complete ($S_0$, $S_1$, $S_2$ and $S_3$) channeled Stokes images.

21 Claims, 24 Drawing Sheets

(56) References Cited

OTHER PUBLICATIONS

Kudenov et al., "White-Light Channeled Imaging Polarimetry Using Broadband Polarization Gratings," Appl. Opt. 50:2283-2293 (2011).

Kudenov et al., "White Light Sagnac Interferometer for Snapshot Polarimetric Imaging," Opt. Exp. 17:22520-22534 (2009).

Luo et al., "Compact and Miniature Snapshot Imaging Polarimeter," Appl. Opt. 47(24):4413-4417 (2008).

Luo, "Snapshot Imaging Polarimeter using Spatial Carrier Frequency," *PhD. Dissertation*, College of Optical Sciences, University of Arizona, (May 2008).

Mujat et. al., "Interferometric Imaging Polarimeter," JOSA A 21(11):2244-2249 (2004).

Oh and Escuti, "Achromatic Diffraction from Polarization Gratings with High Efficiency," Opt. Lett. 33:2287-2289 (2008).

Oh and Escuti, "Numerical Analysis of Polarization Gratings Using the Finite-Difference Time-Domain Method," Phys. Rev. A 76(4):043815 (2007).

Oka and Kaneko, "Compact Complete Imaging Polarimeter Using Birefringent Wedge Prisms," Opt. Exp. 11:1510-1519 (2003).

Oka and Saito, "Snapshot Complete Imaging Polarimeter Using Savart Plates," Proc. SPIE 6295:629508 (2006).

Snik et al., "Spectral Modulation for Full Linear Polarimetry," Appl. Opt. 48(7):1337-1346 (2009).

Tyo et al., "Review of Passive Imaging Polarimetry for Remote Sensing Applications," Appl. Opt. 45(22):5453-5469 (2006).

Walraven R., "Polarization Imagery," Optical Engineering, 20(1):014-018 (1981).

Wang et al., "Anisotropic Wet Etching on Birefringent Calcite Crystal," Appl. Phys. A 81:851-854 (2005).

Wyant, "OTF Measurements with a White Light Source: An Interferometric Technique," App. Opt. 14:1613-1615 (1975).

Courtial et al., "Design of a Static Fourier-Transform Spectrometer with Increased Field of View," *App. Op.* 35(34):6698-6702 (Dec. 1, 2006).

Hirai et al., "Application of Multiple-Image Fourier Transform Spectral Imaging to Fast Phenomena," *Opt. Rev.* 1:205-207 (1994).

Kim et al., "Snapshot imaging spectropolarimeter utilizing polarization gratings," *Proc. of SPIE*, 7086:708603-1-708603-10 (2008).

The Art and Science of Amateur Experimentalism, Sciencemadness Discussion Board, http://www.sciencemadness.org/talk/viewthread.php?tid+13554, downloaded Apr. 15, 2012.

(a)

(b)

(c)

(a)

(b)

(c)

(d)

WHITE LIGHT ACHROMATIC GRATING IMAGING POLARIMETER

CROSS REFERENCE TO RELATED APPLICATIONS

This application is a continuation-in-part of U.S. patent application Ser. No. 13/225,315, filed Sep. 2, 2011, which claims the benefit of U.S. Provisional Application 61/402,767, filed Sep. 3, 2010. This application also claims the benefit of U.S. Provisional Application 61/463,488, filed Feb. 17, 2011. All of the above applications are incorporated herein by reference.

FIELD

The disclosure pertains to imaging polarimeters using polarizing gratings.

BACKGROUND

Polarization images can yield higher contrast than intensity images, providing the opportunity for dramatically improved object identification. Furthermore, incorporation of a polarimeter into a detection system allows for the potential to ascertain the Stokes parameter elements of a scene, thereby giving a complete identification of the polarization state of light reflected or emitted from objects in the scene. From such an analysis, the spatially varying two-dimensional state of polarization (SOP) can be determined.

SOP analysis is a useful technique for object characterization and distinction, particularly for differentiating man made versus natural objects. This is particularly valuable in the thermal infrared; if objects in a scene are emitting close to the background temperature of the environment (i.e., they are close to thermal equilibrium with their environment), then thermal detection typically yields ambiguous results. Addition of polarimetry data can often significantly enhance images of such objects as polarimetry can supply information that is unavailable by intensity imaging. For example, typical long-wavelength infrared (LWIR) intensity images provide little indication of the presence of a vehicle in the shadows of tree, while a polarization image makes the presence of an automobile obvious due to polarization associated with the smooth surfaces of the automobile.

Current techniques for imaging polarimetry include rotating retarder polarimeters. Through a series of sequential measurements, the complete spatial distribution of Stokes parameters in a scene can be determined. This method has several significant limitations. Rotating parts can lead to vibrational and mechanical problems. Images of dynamic scenes can also contain polarization artifacts as a result of combining a series of measurements. Other problems are related to oversampling and spatial synchronization.

Some of the problems with rotating retarder imaging polarimetry can be addressed with "snapshot" systems that do not require dynamic components, but instead take advantage of spatial carrier fringes and Fourier reconstruction techniques in order to provide a complete polarization analysis of a scene. Examples of such approaches are described in Oka and Saito, "Snapshot complete imaging polarimeter using Savart plates," Proc. SPIE 6295:629508 (2008) and Oka and Kaneko, "Compact complete imaging polarimeter using birefringent wedge prisms," Opt. Exp. 11:1510-1519 (2003), both of which are incorporated herein by reference. These approaches use birefringent materials to produce polarization dependent phase differences to produce snapshot images.

One example of such a snapshot system is based on a pair of Savart plates (SPs) introduced in a collimated space in an imaging system. An SP shears incident radiation using crystal birefringence to produce two laterally displaced, orthogonally polarized beams. By combining two orthogonal SPs, an incident optical flux is sheared to create four separate beams. After transmission by an analyzer, these beams are recombined with a lens, resulting in amplitude modulated interference fringes containing state of polarization (SOP) information on the image plane.

While such SP systems are impressive in their snapshot capabilities, they suffer from significant limitations. Due to the reliance on interference effects, the temporal coherence of imaging radiation presents a constraint in that the visibility of the interference fringes is inversely proportional to the spectral bandwidth. For instance, in the LWIR (8-12 µm wavelengths), a fringe visibility of 50% at a mean wavelength of 10 µm requires limiting optical bandwidth $\Delta\lambda_{50\%}\approx 373$ nm, which is a significant constraint with respect to the signal to noise ratio (SNR) of the acquired data. In addition, SP polarimeters require SPs which can be expensive due to the birefringent crystals required. In many wavelength regimes, especially the infrared, the required large crystals (clear apertures>25 mm with thicknesses>10 mm) are either unavailable or prohibitively expensive. Moreover, materials suitable for LWIR use such as CdSe or CdS have birefringences $B=|n_e-n_o|$ that are approximately 10 times less than those of materials suitable for use at visible wavelengths. As a result, thick crystals are needed.

These birefringent material limitations can be avoided through the implementation of a reflective interferometric scheme. Mujat et. al., "Interferometric imaging polarimeter," JOSA A:21:2244-2249 (2004), which is incorporated herein by reference, discloses an interferometric imaging polarimeter based on a modified Sagnac interferometer. In this system, a polarizing beam splitter is used to transmit an input beam into an interferometer, and a phase difference between orthogonal polarizations produced by displacing one of the mirrors in the interferometer is used to create an interference pattern. Irradiance measurements and coherence matrix techniques are then employed to determine the state of polarization from a set of two temporally spaced images. These methods are subject to similar registration problems that plague rotating retarder polarimeters for dynamic scenes.

SUMMARY

White light polarization grating based imaging polarimeters and associated methods are disclosed herein. In some examples, so-called "snapshot imaging polarimeters" are described that operate over broad wavelength ranges, including thermal infrared wavelengths and visible optical wavelengths. Polarizing diffraction gratings are situated to produce a shear between first and second polarization components of a received radiation flux that is proportional to wavelength so that white-light broadband interference fringes are produced. In some examples, complete polarization data for a scene of interest is produced as all four Stokes parameters, while in other examples, only one or several polarization characteristics are determined such as one or more of the Stokes parameters. Stokes parameters are encoded onto a sequence of one or two dimensional spatial carrier frequencies so that a Fourier transformation of a generated fringe pattern enables reconstruction of the Stokes parameter distribution.

In one example, an apparatus comprises at least one polarizing grating configured to produce a dispersion compensated shear between portions of an input light flux associated with first and second polarizations. A detector is situated to receive an output light flux corresponding to a combination of the sheared first and second portions of the input light flux and produce an image signal. An image processor is configured to produce a polarization image based on the image signal. Typically, a polarization analyzer is situated between the at least one grating and the detector. In other examples, the at least one polarizing grating includes two polarizing gratings, wherein the first grating is situated to produce a first shear portion by directing the first polarization along a first direction and the second polarization along a second direction, and the second grating is situated to produce a second shear portion by directing the first polarization directed by the first grating along the second direction and the second polarization directed by the first grating along the first direction. In other examples, the at least one polarizing grating includes a first pair and a second pair of polarizing gratings configured to produce dispersion compensated shear along a first axis and a second axis. Typically, the detector is an array detector. In some examples, the image processor is configured to produce the polarization image based on an amplitude modulation of interference fringes. In further examples, the image processor is configured to select at least one spatial frequency component of the recorded image signal and determine an image polarization characteristic based on an intensity modulation associated with an image signal variation at the selected spatial frequency. Representative image polarization characteristics include one or more or a combination of Stokes parameters $S_0$, $S_1$, $S_2$, and $S_3$. In some alternatives, the polarizing gratings are blazed birefringent gratings and/or liquid crystal gratings. In typical examples, the dispersion compensated shear is proportional to a separation between the first grating and the second grating. In some embodiments, the first grating is situated to direct the first polarization in a + diffraction order and the second polarization in a − diffraction order, and the second grating is configured to effectively direct the first polarization in a − diffraction order and the second polarization in a + diffraction order so as to produce the dispersion compensated shear. In other embodiments, the first grating is situated to direct the first polarization above, and away from, the optical axis and the second polarization below, and away from, the optical axis, and the second grating is configured, in an appropriate manner, to redirect the first and second polarizations to propagate parallel with the optical axis, so as to produce the dispersion compensated shear.

Representative methods comprise receiving an input optical flux and producing a shear between first and second portions of the input optical flux associated with first and second states of polarization that is proportional to a wavelength of the input optical flux by directing the first and second portions to a pair of polarizing gratings. A polarization characteristic of the input optical flux is estimated based on a spatial frequency associated with the shear in an intensity pattern obtained by combining the sheared first and second portions of the input optical flux. In some examples, each of the first and second portions of the incident optical flux are directed to the at least one diffraction grating so as to produce a shear having a magnitude associated with a grating period. In some examples, the shear is inversely proportional to a grating period and directly proportional to a grating order. Typically, the first and second portions are combined with at least one focusing optical element of focal length f, wherein the spatial frequency is inversely proportional to f.

Representative imaging polarimeters include a first polarizing grating configured to diffract portions of an input light flux having a first state of polarization and a second state of polarization in a first direction and a second direction, respectively. A second polarizing grating is configured to receive the diffracted portion from the first polarizing grating and diffract the portions associated with the first state of polarization and the second state of polarization along the second direction and the first direction, respectively, so that the first and second portions propagate displaced from and parallel to each other. A polarization analyzer is configured to produce a common state of polarization of the first and second portions, and a focusing element is configured to combine the first and second portions. A detector is configured to receive the intensity pattern and produce a detected intensity pattern. In some examples, an image processor is configured to produce a polarization image based on the detected intensity pattern. In other examples, the detected intensity pattern is associated with a shear produced by the displacement of the first and second portions.

The foregoing and other features, and advantages of the disclosed technology will become more apparent from the following detailed description, which proceeds with reference to the accompanying figures.

DETAILED DESCRIPTION

Figure 1A:
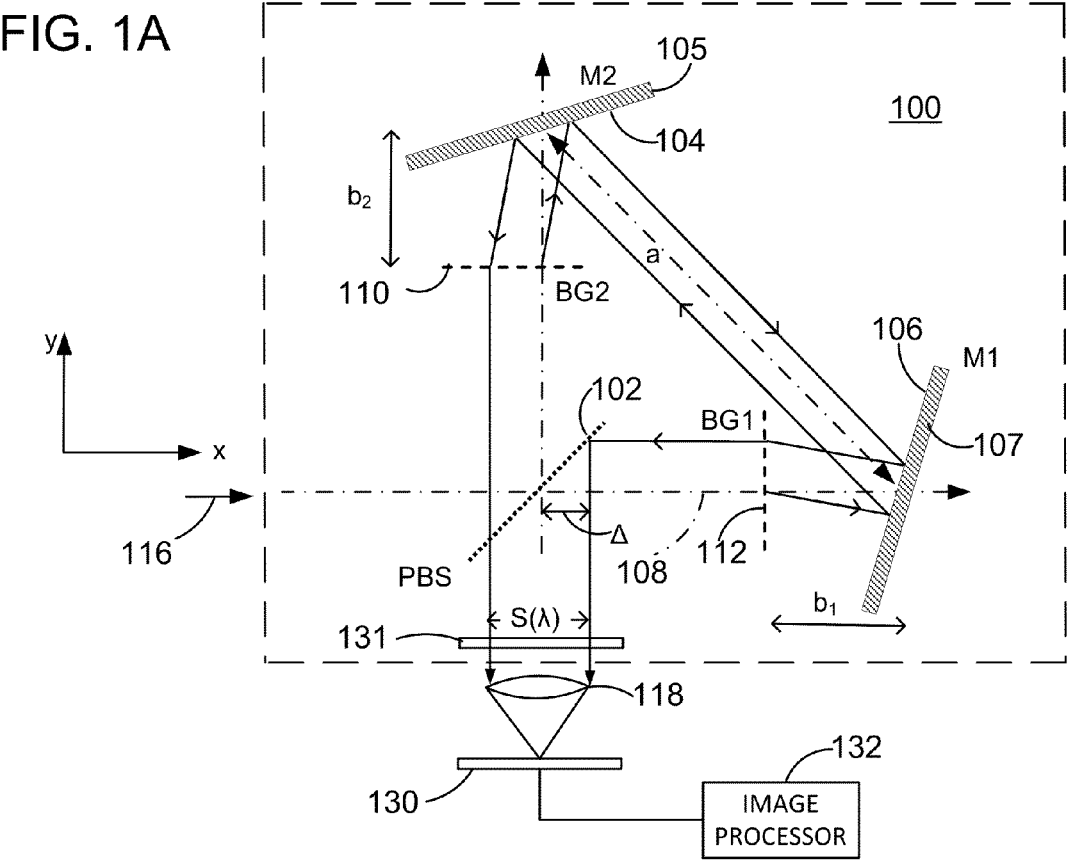
FIG. 1A illustrates a modified Sagnac interferometer configured to produce shear between counter-propagating optical fluxes using two diffraction gratings.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

As used herein, an optical flux refers to electromagnetic radiation in a wavelength range of from about 100 nm to about 100 µm. In some examples, an optical flux has a spectral width that can be as large as 0.5, 1, 2, 5, or 10 times a center wavelength, or can comprises a plurality of spectral components extending over similar spectral bandwidths. Such optical fluxes can be referred to as large bandwidth optical fluxes. Typically, an optical flux is received from a scene of interest and amplitude, phase, spectral, or polarization modulation (or one or more combinations thereof) in the received optical flux is processed based on a detected image associated with a spatial variation of the optical flux which can be stored in one or more computer-readable media as an image file in a JPEG or other format. In the disclosed examples, so-called "snapshot" imaging systems are described in which image data associated with a plurality of regions or locations in a scene of interest (typically an entire two dimensional image) can be obtained in a single acquisition of a received optical flux using a two dimensional detector array. However, images can also be obtained using one dimensional arrays or one or more individual detectors and suitable scanning systems. In some examples, an image associated with the detected optical flux is stored for processing based on computer executable instruction stored in a computer readable medium and configured for execution on general purpose or special purpose processor, or dedicated processing hardware. In addition to snapshot imaging, sequential measurements can also be used. For convenience, examples that provide two dimensional images are described, but in other examples, one dimensional (line) images or single point images can be obtained.

For convenience, optical systems are described with respect to an axis along which optical fluxes propagate and along which optical components are situated. Such an axis is shown as bent or folded by reflective optical elements. In the disclosed embodiments, an xyz-coordinate system is used in which a direction of propagation is along a z-axis (which may vary due to folding of the axis) and x- and y-axes define transverse planes. Typically the y-axis is perpendicular to the plane of the drawings and the x-axis is perpendicular to the y-axis and the z-axis and is in the plane of the drawings.

In representative examples, the imaging polarimetry methods and apparatus disclosed herein can be used to estimate a 2-dimensional spatial Stokes parameter distribution of a scene in order to characterize aerosol size distributions, distinguish manmade targets from background clutter, evaluate distributions of stress birefringence in quality control, evaluate biological tissues in medical imaging, or for other purposes. While in typical examples, image data is evaluated so as to correspond to one or more components of a Stokes vector, data can be processed to obtain other polarization characteristics such as ellipticity or can be based on other representations such as those associated with Jones matrices.

In the disclosed embodiments, interferometers are configured to include diffraction gratings so as to produce a shear between orthogonally polarized components of an input optical flux that is proportional to a wavelength of the input optical flux. For large bandwidth optical fluxes, shear for each spectral component is proportional to a wavelength of the spectral component. A shear between optical fluxes that varies linearly with flux wavelength is referred to herein as a dispersion-compensated shear. In some examples, polarimeters include optical systems that can provide a total shear that includes a dispersion compensated shear and a dispersive shear. As discussed below, a dispersion compensated shear is associated with interference patterns having amplitude modulations at a spatial frequency that is independent of optical wavelength.

Polarization properties of a scene can be conveniently described using a Stokes vector. A scene Stokes vector S(x,y), is defined as:

$$S(x, y) = \begin{bmatrix} S_0(x, y) \\ S_1(x, y) \\ S_2(x, y) \\ S_3(x, y) \end{bmatrix} = \begin{bmatrix} I_0(x, y) + I_{90}(x, y) \\ I_0(x, y) - I_{90}(x, y) \\ I_{45}(x, y) - I_{135}(x, y) \\ I_R(x, y) - I_L(x, y) \end{bmatrix}, \quad (1)$$

wherein x, y are spatial coordinates in the scene, $S_0$ is the total power of the beam, $S_1$ denotes a preference for linear polarization at 0° over linear polarization at 90°, $S_2$ denotes a preference for linear polarization at 45° over linear polarization at 135°, $S_3$ denotes a preference for right circular over left circular polarization states, and I(x,y) refers to optical flux intensity. By measuring all four elements of S(x,y), a complete spatial distribution of the polarization state associated with an scene can be determined. The Stokes vector permits assessment of partially polarized optical fluxes and determination of an extent of polarization as, for example, $$\frac{(S_1^2 + S_2^2 + S_3^2)^{1/2}}{S_0}.$$

As discussed above, some conventional approaches to measuring scene Stokes parameters are based on recording multiple intensity measurements sequentially using different configurations of polarization analyzers. The Stokes parameters can then be calculated using Mueller matrices. However, time-sequential measurements of a rapidly changing scene are susceptible to temporal misregistration. The disclosed methods and apparatus can reduce or eliminate such misregistration errors by acquiring scene image data in a single snapshot. Sequential measurements can be made as well, if desired.

According to representative examples, interferometrically generated carrier frequencies are amplitude modulated with spatially-dependent 2-dimensional Stokes parameters associated with a scene to be imaged. Such methods can be referred to as channeled image polarimetry (CIP) methods. In typical examples, all the Stokes parameters are directly modulated onto coincident interference fringes so that misregistration problems are eliminated, and images can be acquired with readily available lenses and cameras.

Example 1

Symmetric Grating Based Embodiments

For convenient illustration, representative embodiments are described in which diffraction gratings are symmetrically situated in a Sagnac interferometer with respect to reflectors that define counter-propagating optical paths. Following this description, other examples with arbitrary grating placements are described.

With reference to FIG. 1A, a representative Sagnac interferometer 100 includes a polarizing beam splitter (PBS) 102, and reflective surfaces 104, 106 that define an interferometer optical path 108. For convenience, the path 108 is also referred to as an interferometer axis herein. As shown in FIG. 1A, the interferometer axis 108 is folded by the reflective surfaces 104, 106. Blazed transmission gratings (BGs) 110, 112, are situated along the axis 108 at an axial distances $b_1$, $b_2$ from the reflective surfaces 106, 104, respectively. The PBS 102 is configured to receive an input optical flux 116 that is directed along the axis 108 so that portions of the input optical flux 116 are reflected or transmitted to respective reflective surfaces 104, 106 and the associated BGs 110, 112. As shown in FIG. 1A, the reflected and transmitted portions of the input optical flux counter-propagate in the interferometer 100. Typically, the input flux 116 is a collimated optical flux associated with an image scene, and a lens 118 is situated to receive and combine the counter-propagating portions of the input optical flux received from the PBS 102 after transmission by a polarization analyzer 131.

The PBS 102 can be a thin-film based beam splitter such as a polarizing beam splitter cube, a wire grid beam splitter (WGBS), or other polarization dependent beam splitter. The blazed diffraction gratings can be ruled gratings, holographic gratings, or other types of gratings. Reflective surfaces such as the surfaces 104, 106 can be provided as metallic coatings, polished metal surfaces, dielectric coatings, or based on total internal reflection. As shown in FIG. 1A, the reflective surfaces 104, 106 are provided by respective mirrors 105, 107.

The input optical flux 116 is divided into orthogonal polarization components by the polarizing beam splitter 102 and the components are directed along respective arms of the interferometer 100. For example, the portion of the light flux 116 transmitted by the PBS 102 is directed along the axis 108 to the diffraction grating 112 to the reflective surface 106. As shown in FIG. 1A, the reflective surface 106 is situated a distance $b_1$ from the BG 112 measured along the axis 108. The diffraction grating 112 diffracts at least a portion of the incident flux into a single diffraction order at an angle θ, given by a diffraction equation as θ≈mλ/d for small angles, wherein m is an order of diffraction and d is the period of the grating. The resulting diffracted optical flux is then reflected by the reflective surface 106 to the reflective surface 104 and then to the diffraction grating 110 so as to be incident to the diffraction grating 110 at the angle θ and is thereby diffracted so as to propagate parallel to but displaced a distance Δ from the axis 108. The displaced flux is then directed by the PBS 102 to the lens 118. The counter-propagating optical flux (i.e., the flux reflected by the PBS 102) is similarly displaced a distance Δ from the axis 108, but in an opposite direction and is directed to the lens 118 so that the counter-propagating fluxes are combined at a focal plane array detector 130 or other detector. A detected intensity distribution can be stored in one or more computer readable media for processing by an image processor 132.

Figure 10:
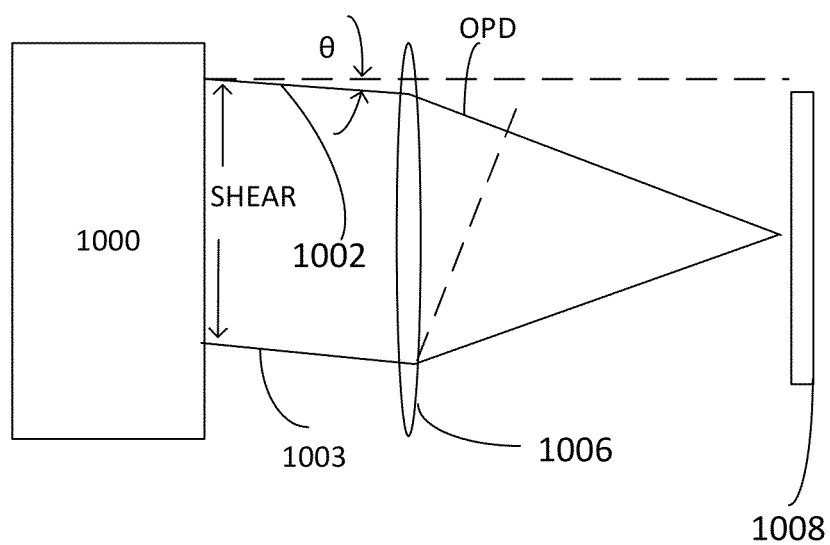
FIG. 10 illustrates determination of an optical path difference (OPD) associated with shear.

Optical path difference (OPD) associated with a focused, sheared optical flux is illustrated in FIG. 10. As shown in FIG. 10, a shearing optical system 1000 such as described above produces shear $S_{shear}$ between flux portions propagating along ray directions 1002, 1003 to a lens 1006 that combines the flux portions at a focal plane array (FPA) 1008 or other detector. For convenient illustration, the lens 1006 is shown as a singlet lens, but in other examples, multi-element lenses, reflective optics, or catadioptric optics can be used. Referring to FIG. 10, $$OPD = S_{shear} \sin(\theta) \approx S_{shear} \theta,$$

for small angle θ. In FIG. 10, θ is depicted as an angle in the object space of the lens 1006 with respect to ray directions 1002, 1003. This assumes that the singlet lens 1006 has an aperture stop that is located at the lens 1006. In this special case, θ is the angle of the chief ray in both object and image space. However, in more sophisticated lens systems, θ is the angle of the chief ray in image space.

When the two sheared portions of the optical flux are combined by the lens, interference fringes are produced on the FPA 1008. This interference can be expressed as $$I(x_i, y_i) = \left\langle \left| \frac{1}{\sqrt{2}} E_x(x_i, y_i, t)e^{-j\phi_1} + \frac{1}{\sqrt{2}} E_y(x_i, y_i, t)e^{-j\phi_2} \right|^2 \right\rangle,$$

where < > represents a time average, $x_i$ and $y_i$ are image-plane coordinates, and $\phi_1$, $\phi_2$, are the cumulative phases along each ray. Expansion of this expression yields $$I(x_i, y_i) = \frac{1}{2} \left\{ \begin{array}{l} (\langle E_x E_x^* \rangle + \langle E_y E_y^* \rangle) + (\langle E_x E_y^* \rangle + \langle E_x^* E_y \rangle)\cos(\phi_1 - \phi_2) + \\ j(-\langle E_x E_y^* \rangle + \langle E_x^* E_y \rangle)\sin(\phi_1 - \phi_2) \end{array} \right\},$$

where $E_x$, $E_y$ are now understood to be functions of image plane coordinates $x_i$ and $y_i$. The phase factors are $$\phi_1 = \frac{2\pi\Delta}{\lambda f_{obj}} x_i \text{ and } \phi_2 = -\frac{2\pi\Delta}{\lambda f_{obj}} x_i.$$

The Stokes parameters are defined from the components of the electric field as $$\begin{bmatrix} S_0 \\ S_1 \\ S_2 \\ S_3 \end{bmatrix} = \begin{bmatrix} \langle E_x E_x^* \rangle + \langle E_y E_y^* \rangle \\ \langle E_x E_x^* \rangle - \langle E_y E_y^* \rangle \\ \langle E_x E_y^* \rangle + \langle E_x^* E_y \rangle \\ j(\langle E_x E_y^* \rangle - \langle E_x^* E_y \rangle) \end{bmatrix}.$$

Re-expressing I using the definitions of the Stokes parameter and $\phi_1$, $\phi_2$, yields $$I(x_i, y_i) = \frac{1}{2} \left[ S_0 + S_2 \cos\left(\frac{4\pi\Delta}{f_{obj}} x_i\right) - S_3 \sin\left(\frac{4\pi\Delta}{f_{obj}} x_i\right) \right]$$

Consequently, the shear modulates $S_2$ and $S_3$ onto a carrier frequency, while $S_0$ remains as an un-modulated component. The carrier frequency U is a function of shear and is given by $$U = \frac{2\pi S(\lambda)}{\lambda f} \quad (2)$$

Fourier filtering can then be used to calibrate and reconstruct the spatially-dependent Stokes parameters over the image plane.

Figure 1B:
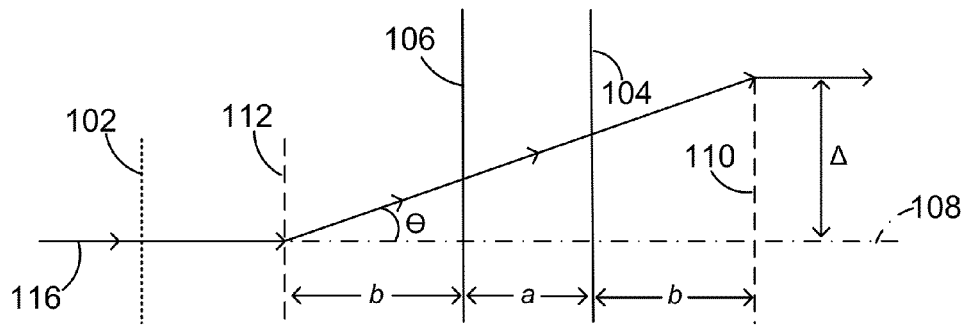
FIG. 1B is an unfolded view of a portion of the interferometer of FIG. 1A.

The determination of the displacement Δ as a function of interferometer geometry is illustrated in the partial unfolded layout of FIG. 1B. The displacement Δ is dependent on the grating-reflective surface axial separations $b_1=b_2=b$ and the axial separation $a$ of the reflective surfaces 104, 106. For small angles, the angular deviation θ from the on-axis path can be expressed as:

$$\theta \approx \frac{m\lambda}{d} \approx \frac{\Delta}{2b+a}, \quad (3)$$

wherein λ is the optical flux and m is a diffraction order. The total shear $S(\lambda)=2\Delta$ can then be expressed as:

$$S(\lambda) = 2\Delta = \frac{m\lambda}{d}(4b + 2a) \quad (4)$$

Thus, the generated shear is directly proportional to wavelength.

The focusing lens 118 combines the sheared optical fluxes at the detector 130 so as to produce fringes (i.e., intensity modulation) at a spatial carrier frequency U based on the total shear, i.e., at a spatial carrier frequency U given by:

$$U = \frac{2\pi S(\lambda)}{\lambda f} = \frac{2\pi m(4b + 2a)}{df}, \quad (5)$$

wherein f is a focal length of the lens 118, and d is a grating period.

In some examples, gratings of different periods and situated to diffract at different orders are used, and the shear is given by:

$$S(\lambda) = 2\Delta = \lambda\left(\frac{m_1}{d_1} + \frac{m_2}{d_2}\right)(2b + a),$$

wherein $m_1$ and $m_2$ are grating diffraction orders, and $d_1$ and $d_2$ are grating periods.

Because the shear is wavelength dependent, the spatial frequency U of the interference fringes which contain the polarization information from the scene is consequently wavelength independent in a paraxial approximation. As a result, high visibility fringes can be obtained for broadband optical sources, regardless of the spatial or temporal coherence of the received optical flux. In addition, a fringe period U can be selected by changing one or more of the reflective surface spacing a, grating spacings $b_1$, $b_2$, grating period d, diffraction order m, and focal length f of the lens 118. In the example of FIG. 1B, the grating-reflective surface spacing is the same for both the gratings 110, 112, but in other examples can be different.

The example of FIGS. 1A-1B is based on a Sagnac interferometer design in which the two optical fluxes to be combined counter-propagate along a common optical path. Thus, such a configuration tends to be resistant to vibration, and input optical fluxes of limited spatial and/or temporal coherence can be used. In other examples, gratings can be situated in interferometers of other configurations, particularly division of amplitude interferometers so as to produce similar shear. For example, diffraction gratings can be used in conjunction with a Mach-Zehnder interferometer to produce shear, although adequate interference fringe visibility may require appreciable optical flux coherence as the Mach Zehnder interferometer does not provide a common optical path. Accordingly, in applications to broad wavelength ranges, common path interferometers generally provide superior results.

In some applications, measurement of all four Stokes parameters is unnecessary. For example, $S_3$ is typically negligible in the thermal infrared and loss of the capability of measuring circular polarization (i.e., $S_3$) is of little consequence. If measurement of $S_3$ is unnecessary, an interferometer system similar to that of FIG. 1A can be provided with an achromatic quarter wave retarder situated with its fast axis at 45 degrees to the axis of the PBS 102 at an interferometer input. Such a configuration permits measurement of $S_0$, $S_1$, and $S_2$. An intensity distribution I(x, y) generated at a focal plane array with such a system can be expressed as:

$$I(x, y) = \frac{1}{2} S_0(x, y) - \frac{1}{2} |S_{12}(x, y)| \cos[2\pi U y - \arg\{S_{12}(x, y)\}] \quad (6)$$

wherein U is the shear generated by the interferometer, $S_{12}=S_1+jS_2$, so that $|S_{12}|$ is a degree of linear polarization and $\arg\{S_{12}\}$ is an orientation of the linear polarization.

Figure 2:
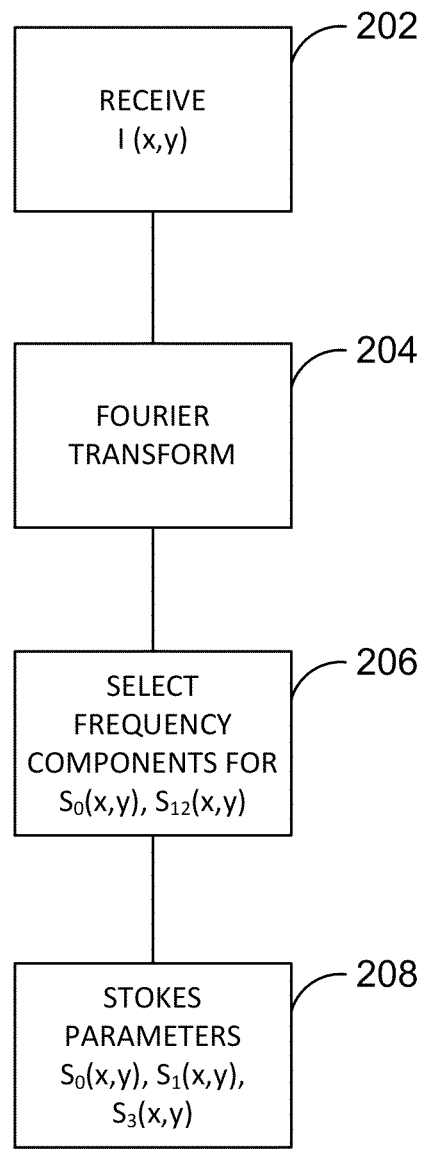
FIG. 2 illustrates an interferometer-based polarimeter configured that includes an input quarter wave retarder and configured for estimation of spatial distributions of Stokes parameters $S_0$, $S_1$, and $S_2$.

Stokes parameters can be extracted from this intensity distribution as shown in FIG. 2. A recorded fringe intensity I(x,y) is received at 202, and at 204, the recorded intensity is Fourier transformed with respect to the shear axis (in the example of FIGS. 1A-1B, a y-axis). At 206, spatial frequency components at zero frequency and at spatial frequency U are identified that are associated with particular combinations of Stokes parameters, such as $S_0(x,y)$ and $S_{12}=S_1+jS_2$ as shown above. At 208, spatial distributions of the Stokes parameters are calculated based on the selected frequency component. Typically, the selected components are inverse Fourier transformed for use in estimating the associated Stokes parameter distributions.

Figure 3:
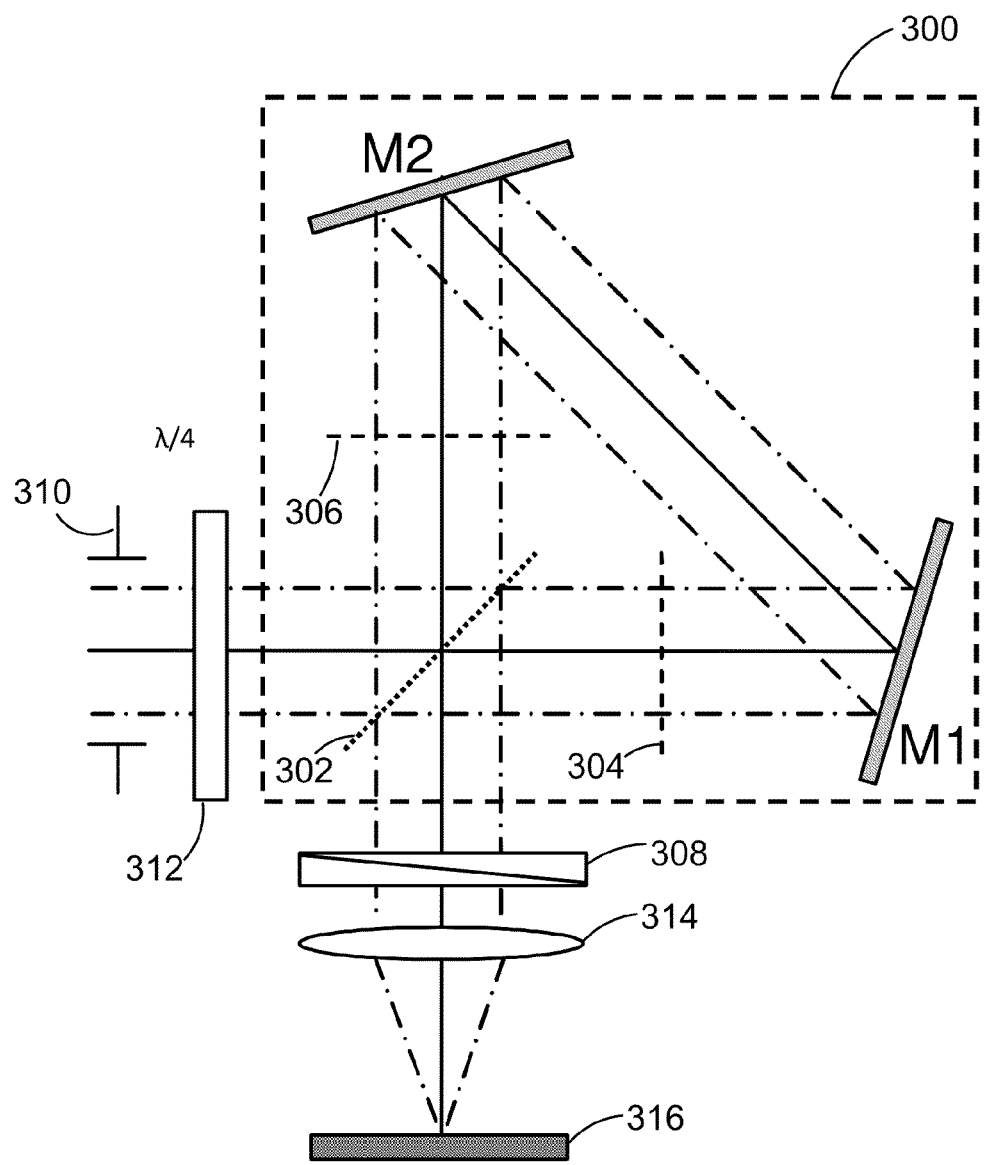
FIG. 3 illustrates an interferometer-based polarimeter that includes an input quarter wave retarder and output linear analyzer configured for estimation of spatial distributions of linear polarization.

A representative interferometer based polarimetry system configured to obtain a linear state of polarization distribution associated with a scene is illustrated in FIG. 3. As shown in FIG. 3, a modified Sagnac interferometer 300 includes an input PBS 302, diffraction gratings 304, 306 and an output linear polarizer 308. An optical flux associated with a scene is directed through an entrance aperture 310 and a quarter wave retarder 312 to the interferometer 300. An objective lens 314 is situated to produce an image that contains modulated polarization information on a focal plane array 316 by combining sheared, counter-propagating optical fluxes.

Example 2

Generalized Dispersion Compensated Sagnac Interferometer Systems

Figure 4A:
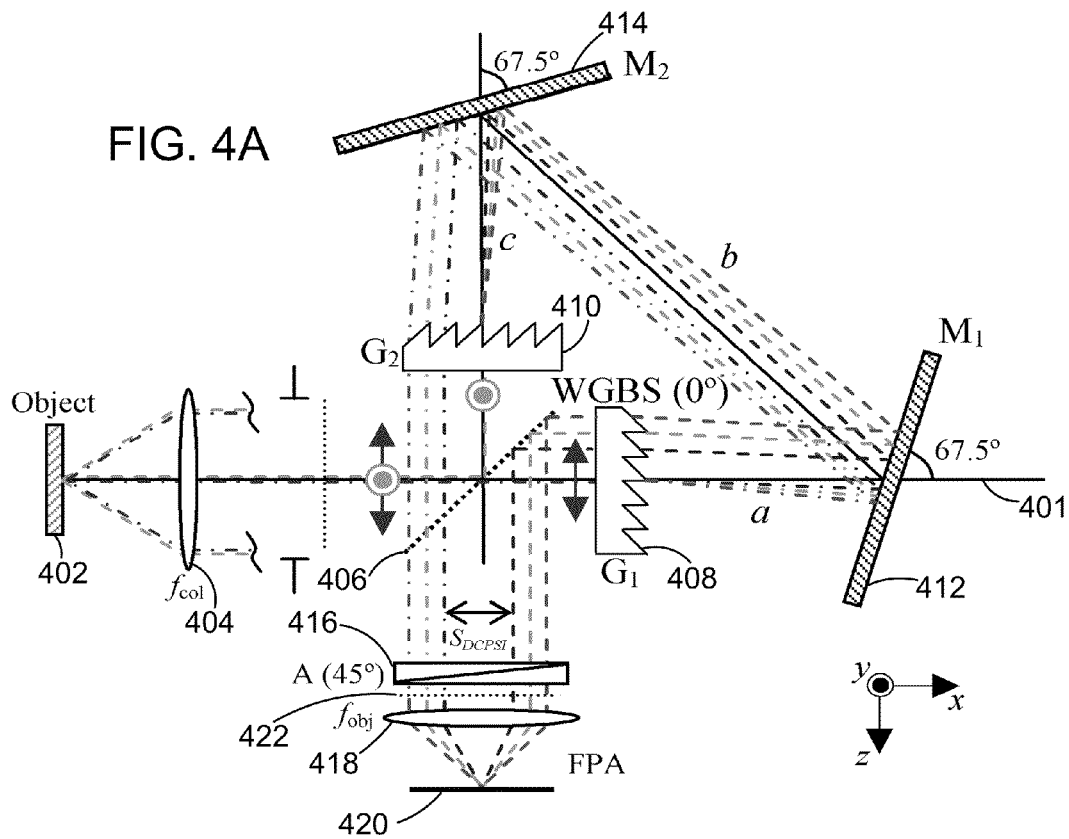
FIGS. 4A-4B illustrate propagation of multiple spectral components in a dispersion compensated interferometer that includes two blazed gratings.
Figure 4B:
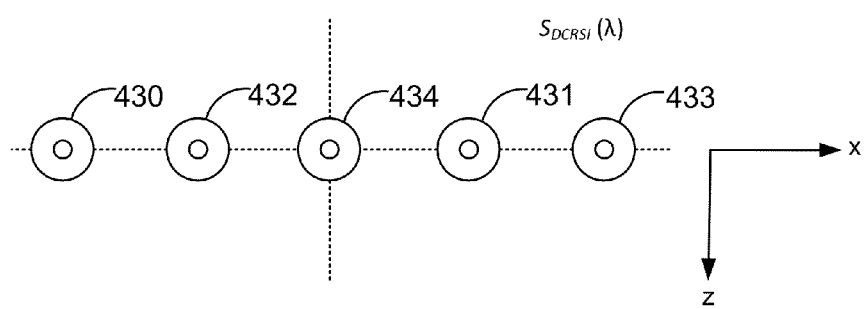

A generalized Sagnac interferometer based polarimeter is illustrated in FIGS. 4A-4B. As shown in FIG. 4A, an object 402 is situated on an axis 401 so that an optical flux from the object 402 is directed to a collimating lens 404 and to a PBS 406. In some examples, the collimating lens 404 can be omitted. A portion of the optical flux in a first polarization state (shown as in the plane of FIG. 4A) is directed through a first grating 408 to mirrors 412, 414, and then to a second grating 410 and the PBS 406. This portion is then directed to an analyzer 416 and focused by an objective lens 418 to a focal plane array 420. A portion of the input optical flux in a second polarization state (shown in FIG. 4A as perpendicular to the plane of FIG. 4A) is oppositely directed and is combined with the counter-propagating flux in the first polarization state at the focal plane array 420 by the lens 418. The combination of the counter-propagating fluxes at the focal plane array produces an interference pattern I(x,y) that can be used to determine one or more of the Stokes parameters or provide other indication of polarization.

For identical diffraction gratings $G_1$ and $G_2$ with grating period d, the shear $S_{DCPSI}$ is given by:

$$S_{DCPSI} = \frac{2m\lambda}{d}(a+b+c) \quad (7)$$

wherein a, b, and c represent the distances between $G_1$ and $M_1$, $M_1$ and $M_2$, and $M_2$ and $G_2$, respectively, and m is a diffraction order. FIG. 4B illustrates the sheared optical flux in a plane 422 that is perpendicular to a z-axis. An undiffracted component of the input flux is situated on axis at 434 while counter-propagating diffracted components associated with a longer and a shorter wavelength are displaced to locations 430, 433 and 432, 431, respectively.

The combined output optical flux as focused by the objective lens (focal length $f_{obj}$) produces an intensity distribution:

$$I_{DCPSI}(x_i, y_i) = \qquad (8)$$

$$\frac{1}{2}\sum_{m=0}^{d/\lambda_{min}} S_0'(m) + \frac{1}{2}\sum_{m=1}^{d/\lambda_{min}}\left[\begin{array}{l}S_2'(m)\cos\left(\frac{2\pi}{f_{obj}}\frac{2m}{d}(a+b+c)x_i\right) - \\ S_3'(m)\sin\left(\frac{2\pi}{f_{obj}}\frac{2m}{d}(a+b+c)x_i\right)\end{array}\right].$$

The intensity distribution $I_{DCPSI}$ is a summation from a diffraction order m=0 to a maximum diffraction order m=(d/$\lambda_{min}$)sin($\pi$/2), wherein $\lambda_{min}$ is a shortest wavelength component of a combined optical flux at the detector. The Stokes parameters $S_0'(m)$, $S_2'(m)$, and $S_3'(m)$ as weighted by grating diffraction efficiency $E(\lambda,m)$ are given by:

$$S_0'(m) = \int_{\lambda_{min}}^{\lambda_{max}} DE^2(\lambda, m) S_0(\lambda) d\lambda, \quad (9)$$

$$S_2'(m) = \int_{\lambda_{min}}^{\lambda_{max}} DE^2(\lambda, m) S_2(\lambda) d\lambda, \quad (10)$$

$$S_3'(m) = \int_{\lambda_{min}}^{\lambda_{max}} DE^2(\lambda, m) S_3(\lambda) d\lambda, \quad (11)$$

wherein $\lambda_m$ in and $\lambda_{max}$ are the minimum and maximum wavelengths in the combined optical flux. Spatial carrier frequencies are given by:

$$U_{DCPSI} = \frac{2m}{df_{obj}}(a+b+c), \quad (12)$$

which is independent of wavelength (i.e., lacks dispersion), permitting white-light interference fringes to be generated. In addition, carrier frequency depends on the diffraction order m, and this dependence can be used in multispectral imaging by, for example, substituting multiple-order gratings for single order gratings. The diffraction efficiency weighted Stokes parameters can be obtained by demodulating $I_{DCPSI}$ with respect to one or more of spatial frequencies $U_{DCPSI}$.

Example 3

White Light Polarimetric Reconstructions in $S_1$ and $S_2$

A quarter wave retarder (QWR) oriented at 45° in front of a simplified channeled spectropolarimeter such as shown in FIG. 4A can be used to measure linear polarization ($S_0$, $S_1$, and $S_2$). The Mueller matrix for a QWR at 45° is $$M_{QWR,45°} = \begin{bmatrix} 1 & 0 & 0 & 0 \\ 0 & 0 & 0 & -1 \\ 0 & 0 & 1 & 0 \\ 0 & 1 & 0 & 0 \end{bmatrix}$$

Multiplication of this matrix by an arbitrary incident Stokes vector yields $$S_{out} = M_{QWR,45°}[S_0 S_1 S_2 S_3]^T = [S_0 -S_3 S_2 S_1]^T.$$

Therefore, the QWR converts any incident linear horizontal or vertical polarization states ($S_1$) into circular polarization ($S_3$) and vice versa. Consequently, with an included QWR, the detected intensity pattern becomes $$I_{DCPSI}(x_i, y_i) = \frac{1}{2}\sum_{m=0}^{d/\lambda_1} S_0'(m) + \frac{1}{2}\sum_{m=1}^{d/\lambda_1}\left[\begin{array}{l}S_2'(m)\cos\left(\frac{2\pi}{f_{obj}}\frac{2m}{d}(a+b+c)x_i\right) - \\ S_1'(m)\sin\left(\frac{2\pi}{f_{obj}}\frac{2m}{d}(a+b+c)x_i\right)\end{array}\right],$$

wherein $S_1'(m)$ is analogous to $S_3'(m)$, and is defined as $$S_1'(m) = \int_{\lambda_1}^{\lambda_2} DE^2(\lambda, m)S_1(\lambda)d\lambda.$$

Inverse Fourier transformation of channels $C_0$ (zero frequency component) and $C_1$ (component at frequency $U_{DCPSI}$) yields $$\mathfrak{F}^{-1}[C_0] = \frac{S_0'(1)}{2}$$

$$\mathfrak{F}^{-1}[C_1] = \frac{1}{4}(S_2'(1) + jS_1'(1))\exp(j2\pi U_{DCPSI}x_i),$$

assuming that the m=1 diffraction order is dominant. Thus, a full linear polarization measurement including the degree of linear polarization (DOLP) and its orientation can be calculated from a single interference pattern. The DOLP and its orientation can be determined as:

$$DOLP = \frac{\sqrt{S_1^2 + S_2^2}}{S_0}$$

$$\phi = \frac{1}{2}\text{atan}\left(\frac{S_2}{S_1}\right).$$

Example 4

Dual-Band Snapshot Imaging Polarimeter

Figure 5:
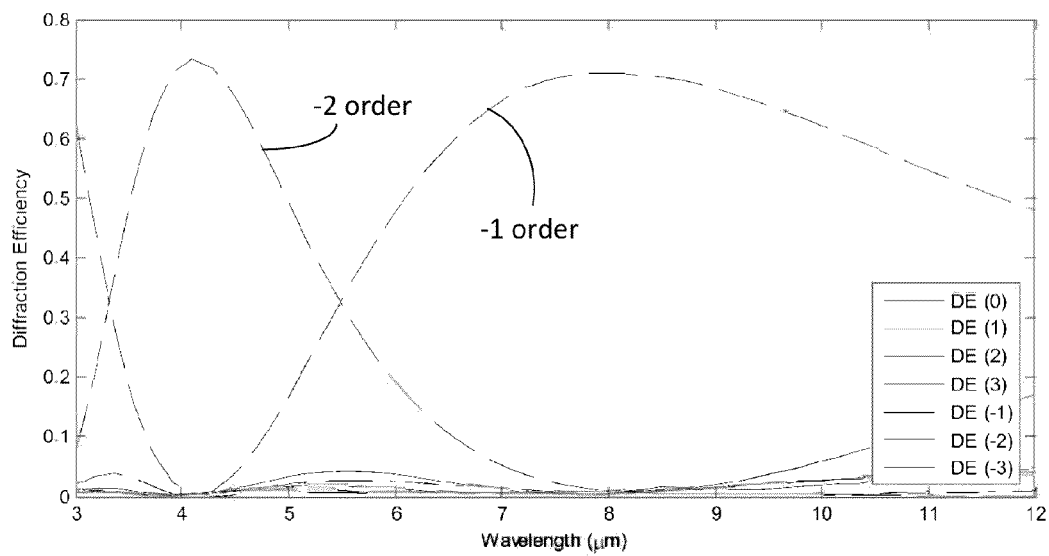
FIG. 5 is a graph of theoretical diffraction efficiency for a blazed grating designed for a wavelength of roughly 8 µm on a ZnSe substrate. Diffraction efficiencies for the 0, +/−1, +/−2, and +/−3 orders are shown.

Blazed gratings can have high diffraction efficiency into a single diffraction order at a design wavelength. At other wavelengths, a blazed grating can produce substantial diffraction into a plurality of diffraction orders. In some examples, polarization analysis can be provided in two or more wavelength bands that are nearly integer multiples of each other. For example, analysis in a combination of a midwavelength infrared band (MWIR) of about 3-5 μm and a long wavelength infrared band (LWIR) of about 8-12 μm can be provided. These wavelength bands are close to an integer separation in optical path difference so that a blazed grating designed for a +1 order at a wavelength of 8 μm will have maximum efficiency at 8 μm in the +1 order, 4 μm in the +2 order, 2 μm in the +3 order, etc. Therefore, a grating can be chosen to be suitable for both MWIR and LWIR bands. Diffraction efficiencies for a representative grating having a design wavelength of 8 μm at various diffraction orders is shown in FIG. 5. As shear is proportional to diffraction order, such a configuration produces twice as much shear in the MWIR than in the LWIR so that fringe spatial frequency in the MWIR is twice that in the LWIR. MWIR and LWIR image contributions can be separated by demodulation of the fringes based on corresponding fringe spatial frequencies. Other diffraction orders can also appear in the detected fringes, and these can be reduced or removed based on their differing spatial frequencies.

Example 5

Deep Grating Multispectral Snapshot Imaging Spectrometer

Figure 6:
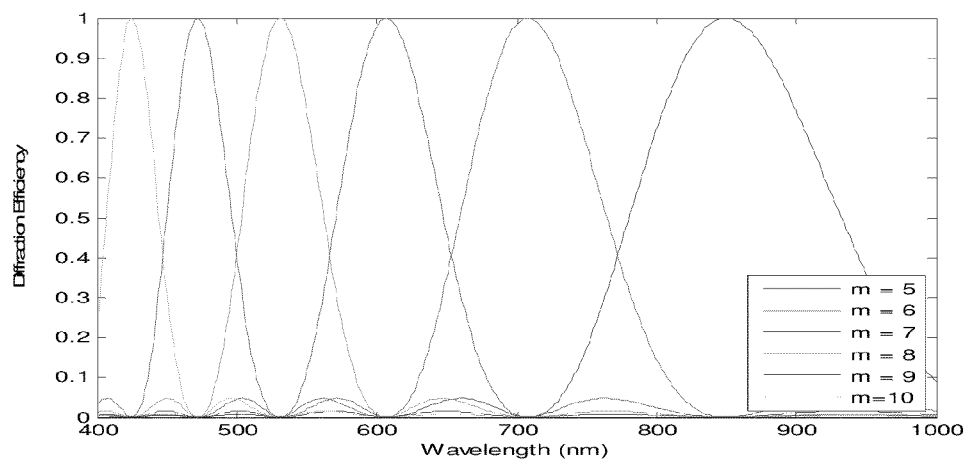
FIG. 6 is a graph of diffraction efficiency for a multiple order "deep" blazed diffraction grating having a 2.12 µm grating depth.
Figure 7A:
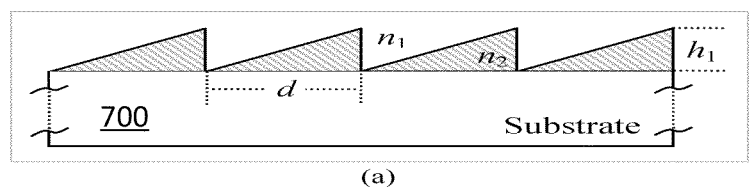
FIGS. 7A-7B illustrate single order and multiple order blazed gratings.
Figure 7B:
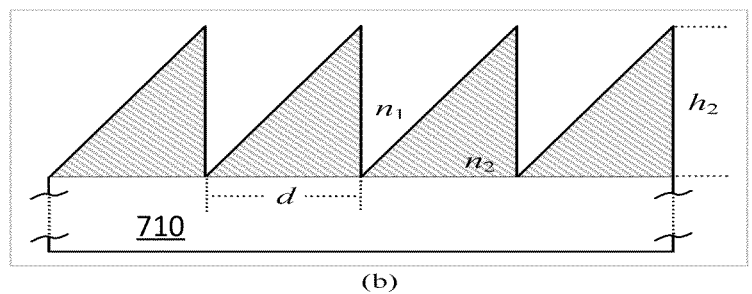

As shown above, in dual-band operation, an MWIR carrier frequency generated by a second order diffraction order is twice that of the LWIR carrier frequency generated by a first diffraction order. In additional examples, scene spatial information over a wide wavelength range can be modulated onto carrier frequencies that are spectrally dependent so that polarization information or spectral information can be extracted. In such applications, a 'deep', or multiple-order blazed grating (MBG) having multiple diffraction orders spanning the wavelength region of interest can be used. FIG. 6 is a graph of diffraction efficiency of such an MBG for a wavelength range spanning the visible and near infrared spectrum for diffraction orders 5-10. FIGS. 7A-7B are cross-sectional views of a single order BG 700 and an MBG 710. Both are defined by periodic steps of triangular cross-section between refractive indices $n_1$ and $n_2$ with period d, but the BG 700 has a height $h_1$ which is smaller than a height $h_2$ of the MBG 710.

Theoretical diffraction efficiency (DE) for an ideal blazed grating at a wavelength λ in a diffraction order m can be calculated as $$DE(\lambda, m) = \text{sinc}^2\left(\frac{m - OPD}{\lambda}\right), \tag{13}$$

wherein $$OPD = h(n_1 - n_2), \tag{14}$$

and h is groove height, OPD is an optical path difference, and $n_1$, $n_2$ are indices of refraction for incident medium and blaze medium, respectively.

Example 6

Back-to-Back Grating Multispectral Snapshot Imaging Spectrometer

Figure 8A:
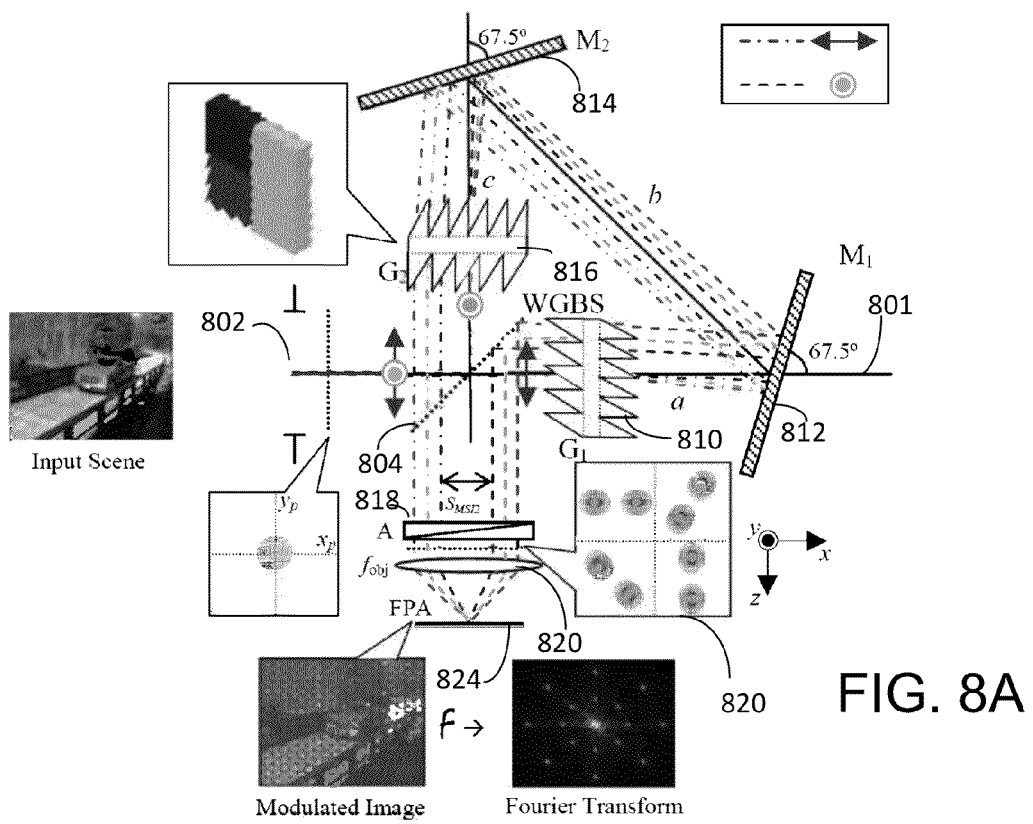
FIG. 8A illustrates a Sagnac interferometer based imaging polarimeter that includes multiple-order blazed gratings (MBGs) situated to provide multiple diffraction orders in two directions.

In other examples, multispectral polarimeters can include back-to-back gratings or grating assemblies with grating segments of various periods and orientation. With reference to FIG. 8A, a multispectral imaging polarimeter 800 includes an aperture 802 and a PBS 804 situated along an axis 801 and configured to receive an input optical flux, typically an optical flux associated with a two dimensional scene. The PBS 804 is situated to transmit a first polarization component of the input output flux to a first multi-wavelength blazed grating (MBG) 810, mirrors 812, 814, a second MBG 816 for transmission by the PBS 804 to a linear polarizer 818. An objective lens 820 focuses the received flux onto a focal plane array detector (FPA) 824. The PBS 804 is situated to reflect a second polarization component of the input output flux to the second MBG 816, mirrors 814, 812, the first MBG 810 for reflection by the PBS 804 to the linear polarizer 818. The objective lens 820 focuses the received flux onto the FPA 824 in combination with the flux transmitted by the PBS 804. As a result, a fringe pattern is formed on the FPA 824, with spatial carrier frequencies proportional to diffraction order.

Figure 8B:
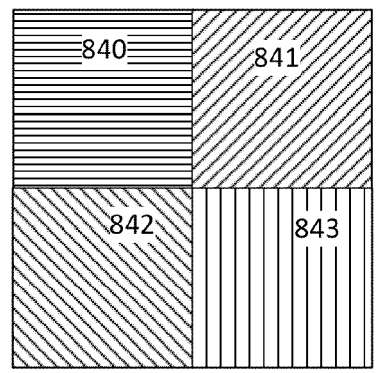
FIG. 8B illustrates a grating assembly that provides multiple diffraction orders in a plurality of directions.

The MBGs 810, 812 can be deep gratings as described above and shown in FIG. 7B. Such gratings produce fringe modulations at a variety of frequencies for corresponding spectral components of the scene optical flux based. Back to back gratings or multi-segmented gratings can be used. In the example of FIG. 8A, the MBGs 810, 812 are multi-segmented gratings as shown in FIG. 8B. For example, the MBG 810 can comprise grating segments 840-843 each having a different orientation and grating period. The grating segments can be low order blazed gratings or MBGs as well. The grating segments 840-843 can produce shears of different magnitudes and in different directions. In one example, an intensity distribution 820 is illustrated in a plane perpendicular to a z-axis (direction of optical flux propagation) and situated between the lens 820 and the analyzer 818. Shear of the input optical flux to locations displaced along both the x-axis and the y-axis and combinations of such shears is apparent.

If a linear polarizer is inserted with its axis at 45° with respect to the x-axis, then the Stokes vector incident on the PBS 804 is given by:

$$S_{WGBS} = \frac{1}{2}\begin{bmatrix} 1 & 0 & 1 & 0 \\ 0 & 0 & 0 & 0 \\ 1 & 0 & 1 & 0 \\ 0 & 0 & 0 & 0 \end{bmatrix}\begin{bmatrix} S_{0,inc} \\ S_{1,inc} \\ S_{2,inc} \\ S_{3,inc} \end{bmatrix} = \begin{bmatrix} S_{0,inc} + S_{2,inc} \\ 0 \\ S_{0,inc} + S_{2,inc} \\ 0 \end{bmatrix}. \quad (15)$$

$S_0$, $S_{1,inc}$, $S_{2,inc}$, and $S_{3,inc}$ are the incident Stokes parameters at the linear polarizer and are implicitly dependent upon wavelength ($\lambda$). Substituting the values from $S_{WGBS}$ for the Stokes parameters from the equations above yields:

$$S_0'(m) = S_2'(m) = \int_{\lambda_{min}}^{\lambda_{max}} DE^2(\lambda, m)[S_{0,inc}(\lambda) + S_{2,inc}(\lambda)]d\lambda, \quad (16)$$

Substituting the values for $S_0'(m)$, $S_2'(m)$, and $S_3'(m)$ yields the intensity pattern:

$$I_{MSI}(x_i, y_i) = \frac{1}{2}\sum_{m=0}^{Ce[\lambda_1/\lambda_{min}]} [S_0''(m)] + \quad (17)$$

$$\frac{1}{2}\sum_{m=1}^{Ce[\lambda_1/\lambda_{min}]} \left[ S_0''(m)\cos\left(\frac{2\pi}{f_{obj}}\frac{2m}{d}(a+b+c)x_i\right) \right],$$

wherein $$S_0''(m) = \int_{\lambda_{min}}^{\lambda_{max}} DE^2(\lambda, m)[S_{0,inc}(\lambda) + S_{2,inc}(\lambda)]d\lambda. \quad (18)$$

It should be noted that the dominant orders experimentally observed in the system correspond to the ceiling (Ce) of $\lambda_1/\lambda_{min}$, where $\lambda_1$ is the first order blaze wavelength of the diffraction grating. This changes the maximum limit of the summation from $d/\lambda_{min}$ to $Ce[\lambda_1/\lambda_{min}]$.

Example 7

Combined Gratings/Reflectors

Figure 9:
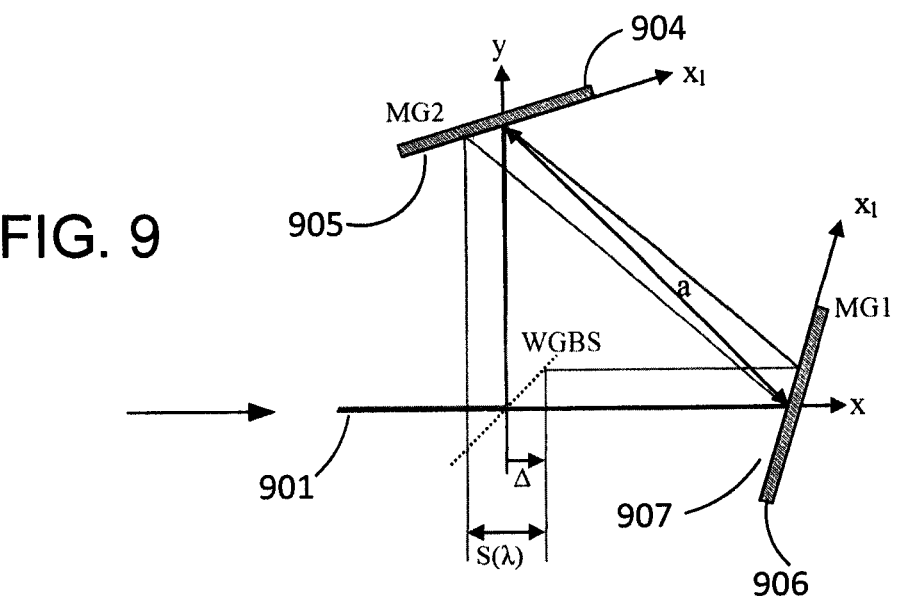
FIG. 9 illustrates a Sagnac interferometer system that includes diffraction gratings formed on mirror surfaces.

With reference to FIG. 9, a Sagnac interferometer based polarimeter includes mirrors 904, 906 that include diffraction gratings 905, 907 at respective mirror surfaces. Shear is dependent on pupil position in the y-plane due to the variation in separation along the mirror local x-axes $x_l$. The on-axis shear is:

$$S(\lambda) = \frac{2am\lambda}{d} \quad (19)$$

wherein a is a separation between mirrors 904, 906 along an optical axis 901 and is a function of $x_l$. To correct or compensate, a slowly varying chirp can be added to the blazed gratings on the mirrors 904, 906 such that a grating period d depends upon $x_l$. With such a modification, shear S can be constant or nearly so over the entire pupil.

Example 8

Serial or Parallel Sagnac Interferometer Systems

Figure 11A:
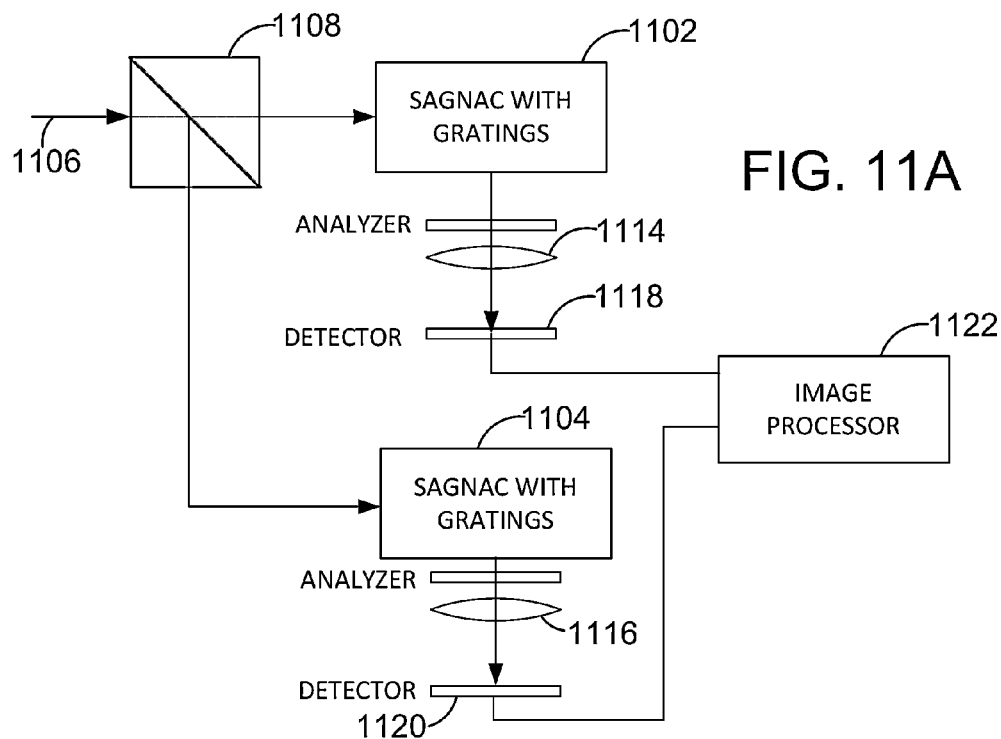
FIGS. 11A-11B illustrate polarimeters based on parallel or serial arrangements of Sagnac interferometers.
Figure 11B:
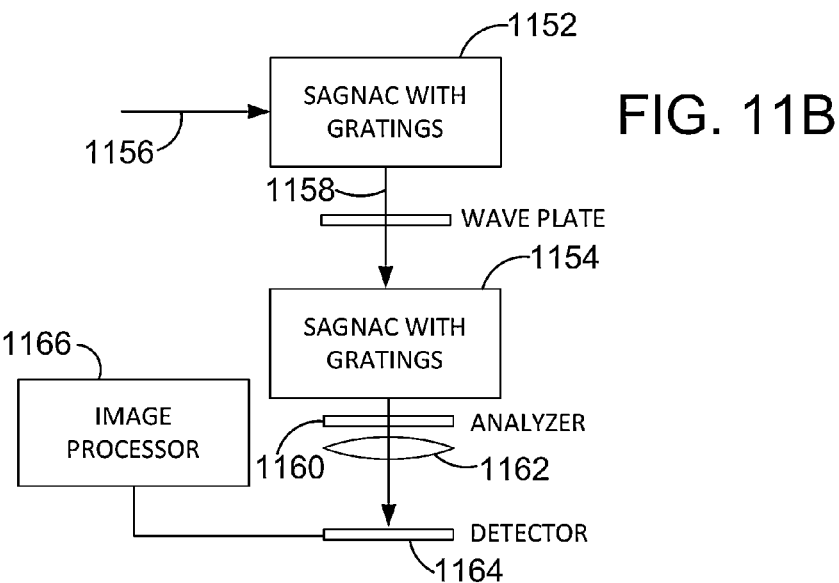

In some applications, determination of all four Stokes parameter may be desirable. Representative systems are illustrated in FIGS. 11A-11B. Referring to FIG. 11A, first and second Sagnac interferometer systems 1102, 1104 that include diffraction gratings as described in the examples above are configured to receive respective portions of an input optical flux 1106 from a beam splitter 1108. Typically, the beam splitter 1108 is substantially polarization independent, and can be provided as a plate beam splitter or other suitable optical element. The Sagnac interferometers direct sheared optical fluxes to respective polarizers (or other polarization components) 1110, 1112, lenses 1114, 1116, and array detectors 1118, 1120, respectively. An image processor 1122 receives detected interference signals from the array detectors 1118, 1120, respectively, and produces estimates of some or all Stokes parameters.

FIG. 11B illustrates a representative serial configuration that permits estimation of all four Stokes parameters. This configuration includes Sagnac interferometer systems 1152, 1154 situated in series. The interferometer 1152 is situated to receive an input optical flux 1156 and produce a sheared output flux 1158 that is directed to a retarder such as a quarter waver retarder or half wave retarder or other retarder and directed to the interferometer 1154. The interferometer 1154 provides additional shear and the sheared output is directed to an analyzer 1160, a lens 1162, and an array detector 1164. A detected interference pattern is evaluated in an image processor 1166 that is configured to identify one or more spatial frequency components in the detected interference pattern so as to provide estimates of one or more Stokes parameters.

The interferometers 1152, 1154 can be configured so as to produce interference patterns at different spatial frequencies based on, for example, diffraction grating periods, diffraction orders, or grating or mirror spacings. Modulations imposed by the interferometers can be detected based on these differing spatial frequencies. Alternatively, the interferometers 1152, 1154 can be configured to provide modulations at spatial frequencies associated with different spatial directions. For example, a first interferometer can provide an x-modulation and a second interferometer can provide a y-modulation that can be at the same or different spatial frequency so that modulation associated with the Stokes parameters can be identified based on either direction or spatial frequency or both.

Example 9

Calcite Blazed Grating Pairs

Figure 12:
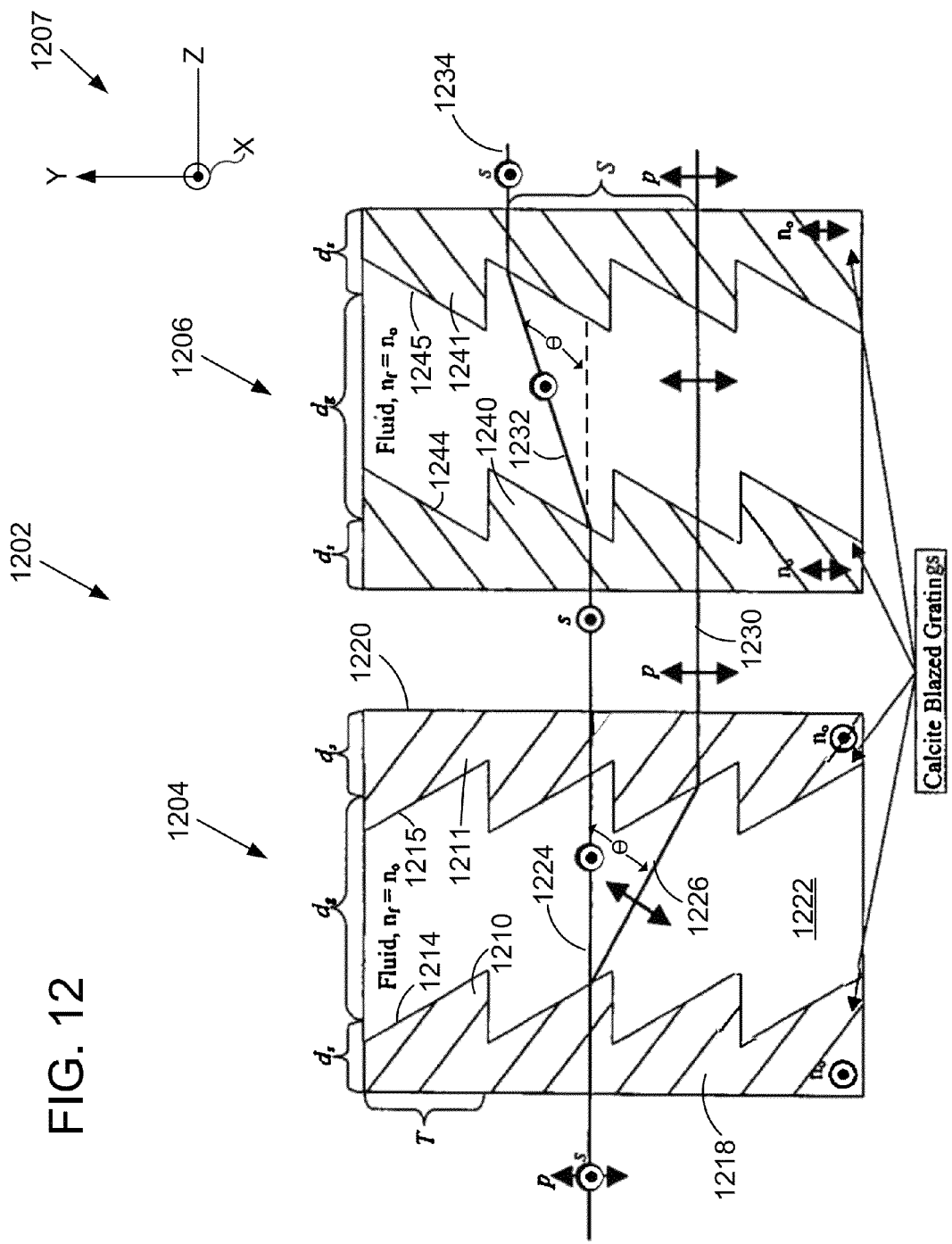
FIG. 12 is a schematic diagram of blazed birefringent grating pairs situated to produce a compensated shear.

Imaging or other polarimeters suitable for use white light or other broadband radiation can be based on polarization dependent diffraction gratings. Such polarimeters can produce modulated fringe patterns from which one or more Stokes images can be extracted as described above with Sagnac interferometer produced shear. FIG. 12 illustrates a portion of a representative optical system that includes a grating pair 1202 that includes a first grating 1204 and a second grating 1206. For convenience, the grating pair 1202 is described with reference to an orthogonal xyz-coordinate system 1207. A Y-axis and a Z-axis are shown in the plane of the drawing, and an X-axis is perpendicular to the plane of the drawing. The grating 1204 includes first and second birefringent subgratings 1210, 1211 having shaped ("blazed") surfaces 1214, 1215, respectively, that are periodic along the Y-axis. As shown in FIG. 12, the subgratings 1210, 1211 also include planar surfaces 1218, 1220 that can serve as optical input/output surfaces. These surfaces area typically planar, but non-planar surfaces can be used. The surfaces 1214, 1215 can be formed by any convenient process such as ruling or etching. In one convenient implementation, the surfaces 1214, 1215 are formed using anisotropic etching of a birefringent material such as calcite. The shaped surfaces 1214, 1215 are situated so as to be spaced apart and facing each other along an axis 1220. In addition, the surfaces 1214, 1215 are optically coupled with an index matching material 1222 such as an index matching liquid.

The birefringent subgratings 1210, 1211 can be formed of a uniaxial or biaxial material. The shaped surface 1214 and the subgrating 1210 are configured so that a selected input polarization (shown in FIG. 12 as an s-polarization) propagates in the subgrating 1210 and experiences a first index of refraction $n_o$ as so-called "ordinary" ray. A refractive index of the index matching material 1222 is selected to be substantially equal to $n_o$ so that an input beam corresponding to an "ordinary ray" is undiffracted and unrefracted at the shaped surface 1214. As shown in FIG. 12, the subgrating 1210 is configured so that an X-directed linear polarization is undiffracted by the shaped surface 1214 and propagates along a path 1224 that is substantially unchanged by the shaped surface 1214. In contrast, an orthogonal polarization (a Y-directed linear polarization, referred to as a p-polarization in FIG. 12) is diffracted/refracted based on a refractive index difference between the refractive index of the matching material 1222 and an extraordinary refractive index $n_e$ in the subgrating 1210 and propagates along a path 1226. The subgrating 1211 and the shaped surface 1215 are similarly configured so that the ordinary polarization exits the grating 1204 along the path 1226 and the extraordinary polarization is diffracted/refracted by the shaped surface 1215 so as to exit the grating 1204 along a path 1230 that is substantially parallel to and offset from the path 1226 associated with the ordinary ray.

The displaced ordinary and extraordinary beams could be combined with a lens and at least partially projected into a common state of polarization with a polarizer that is unaligned with either to produce interference fringes. Unfortunately, the displaced beams are associated with significant phase delays so that broadband illumination would produce no fringes or fringes with limited visibility. To compensate, the second grating 1206 is configured similarly to the first grating 1204, but with birefringent subgratings 1240, 1241 arranged so that the ordinary beam is diffracted/refracted along path 1232 by a shaped surface 1244 and then along a path 1234 by a shaped surface 1245. Thus, the same diffraction angles are encountered by both polarization components, although in different polarizing gratings. As a result, orthogonally polarized beams exit the second grating 1206 along parallel, displaced paths 1230, 1234. With each polarization displaced, broadband or white light fringes can be obtained.

The shear S between the paths 1230, 1234 can be obtained as $S=2 d_g \tan \theta \approx 2 d_g \lambda/T$, wherein $\lambda$ is a wavelength, $\theta$ is a diffraction angle, m is a diffraction order, T is a grating period, and $d_g$ is separation of the shaped surfaces 1214, 1215 or 1244, 1245. As discussed above, a shear that is proportional to wavelength results in a spatial carrier frequency that is independent of wavelength, and thus suitable for use with broadband radiation.

In the example of FIG. 12, grating periods and shaped surface separations are the same for both the first and second gratings 1204, 1206, but in other examples, different spacing and periods can be used. Typically, differing periods and/or spacings tend to produce less visible fringes with broadband radiation. The configuration of FIG. 12 produces a compensated shear suitable for use with broadband radiation.

Example 10

Dual Calcite Blazed Grating Pairs for X- and Y-Displacements

Figure 13:
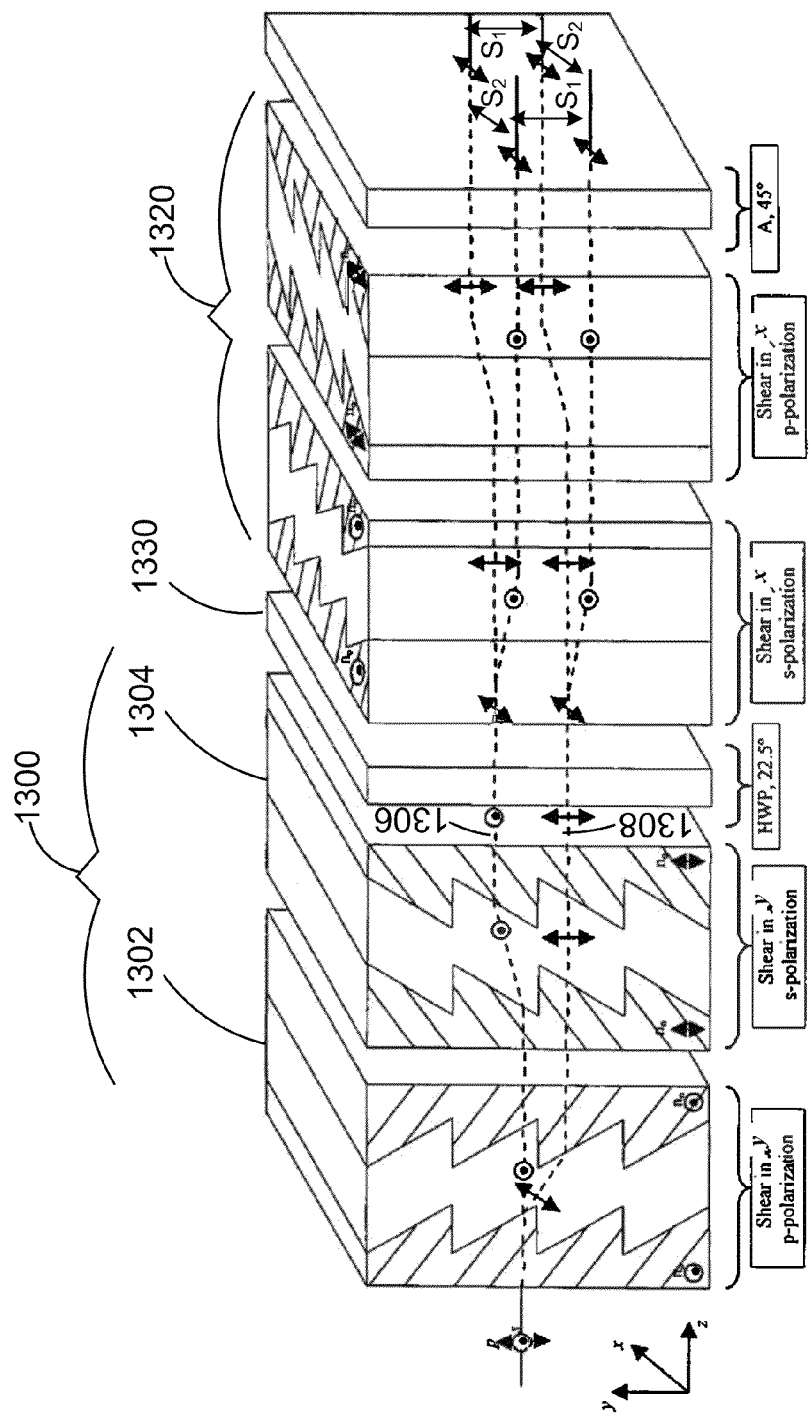
FIG. 13 is a is a schematic diagram of two pairs of blazed birefringent gratings configured to produce four beams based on compensated shears in an X-direction and a Y-direction.

Referring to FIG. 13, a first grating pair 1300 includes first and second calcite blazed gratings 1302, 1304 such as those described above and configured to produce compensated shear along a Y-direction so that an s-polarized beam 1306 and a p-polarized beam 1308 have a compensated shear $S_Y$ along a Y-direction. One or both of the beams 1306, 1308 can be sheared in an X-direction with a second grating pair 1320 that includes first and second calcite blazed gratings 1322, 1324 oriented orthogonal to those of the first grating pair 1300. The second grating pair 1320 can be configured to produce a shear $S_X$ that is the same or different that the shear $S_Y$ based on grating periods or spacings.

A half-waveplate (HWP) 1330 is situated with a fast or slow axis at about 22.5 degrees with respect to the X-axis or the Y-axis and between the first grating pair 1300 and the second grating pair 1320. The HWP 1330 rotates the plane polarization of each of the beams 1306, 1308 by 45 degrees so each of the beams 1306, 1308 is further sheared in an X-direction by the second grating pair 1320. Thus, four sheared beams are produced. To produce interference fringes, a polarization analyzer 1340 is situated so as to transmit linear polarization along an axis at 45 degrees with respect to the X-axis or the Y-axis. The corresponding polarized beams can then be focused to produce interference fringes.

Example 11

Dual Calcite Blazed Grating Pairs for Linear SOP Imaging

Figure 14:
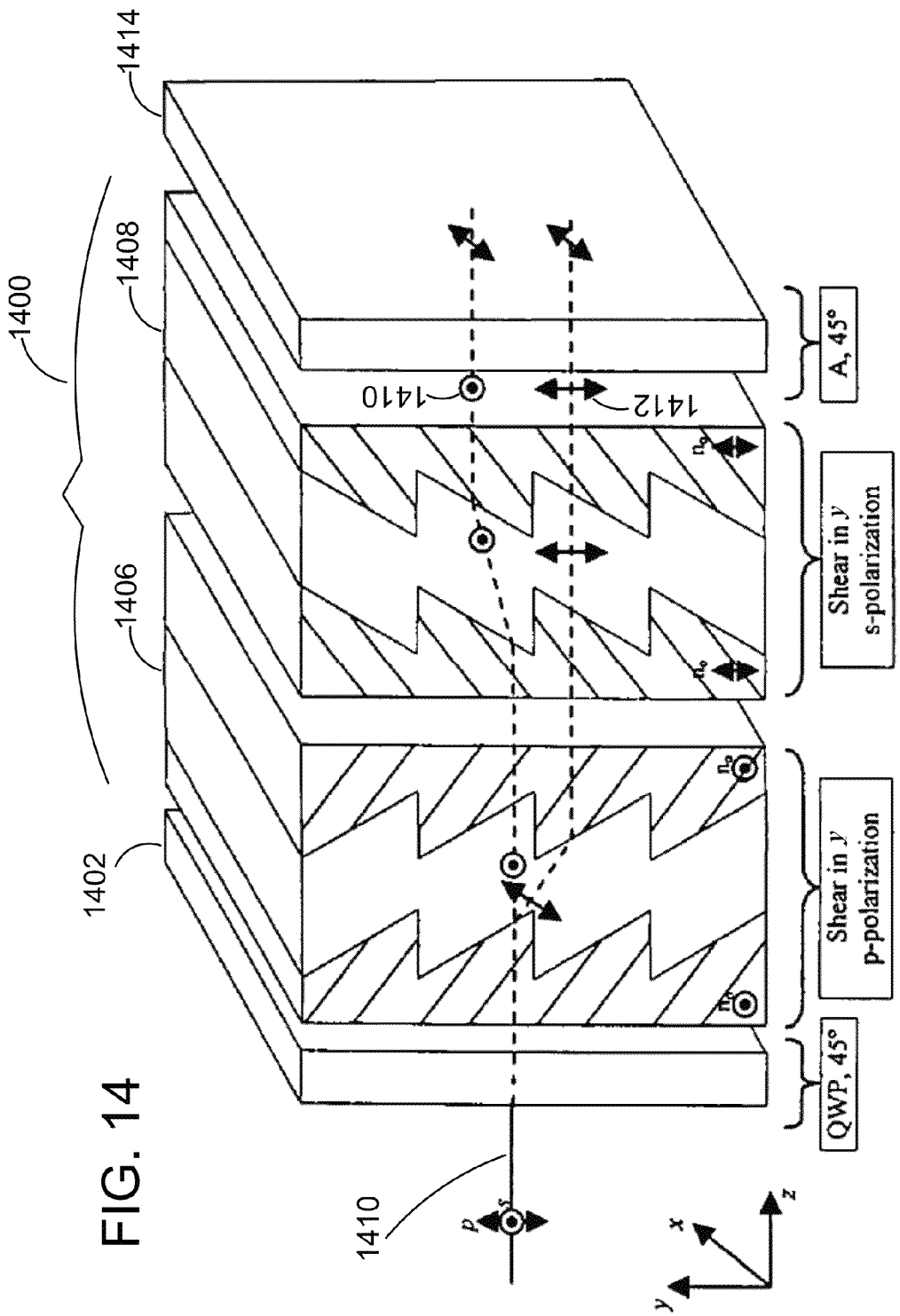
FIG. 14 illustrates production of a shear with a polarizing grating pair.

FIG. 14 is a representative example of a birefringent grating pair 1400 configured for linear polarization measurements. A quarter waveplate 1402 and first and second gratings 1406 and 1408 are situated along an axis 1410. An analyzer 1414 is situated with a fast axis at 45 degrees with respect to the states of polarization of the sheared beams 1410, 1412. Measurements of Stokes parameters $S_1$ and $S_2$ can be obtained, and the assembly can be located in a focal plane of a 4f imaging system (i.e., an imaging system with object and image distances of twice a focal length) or in front of a single lens/FPA combination for imaging of distant objects.

Example 12

Liquid Crystal Polarization Grating (PG) Pairs

Figure 15:
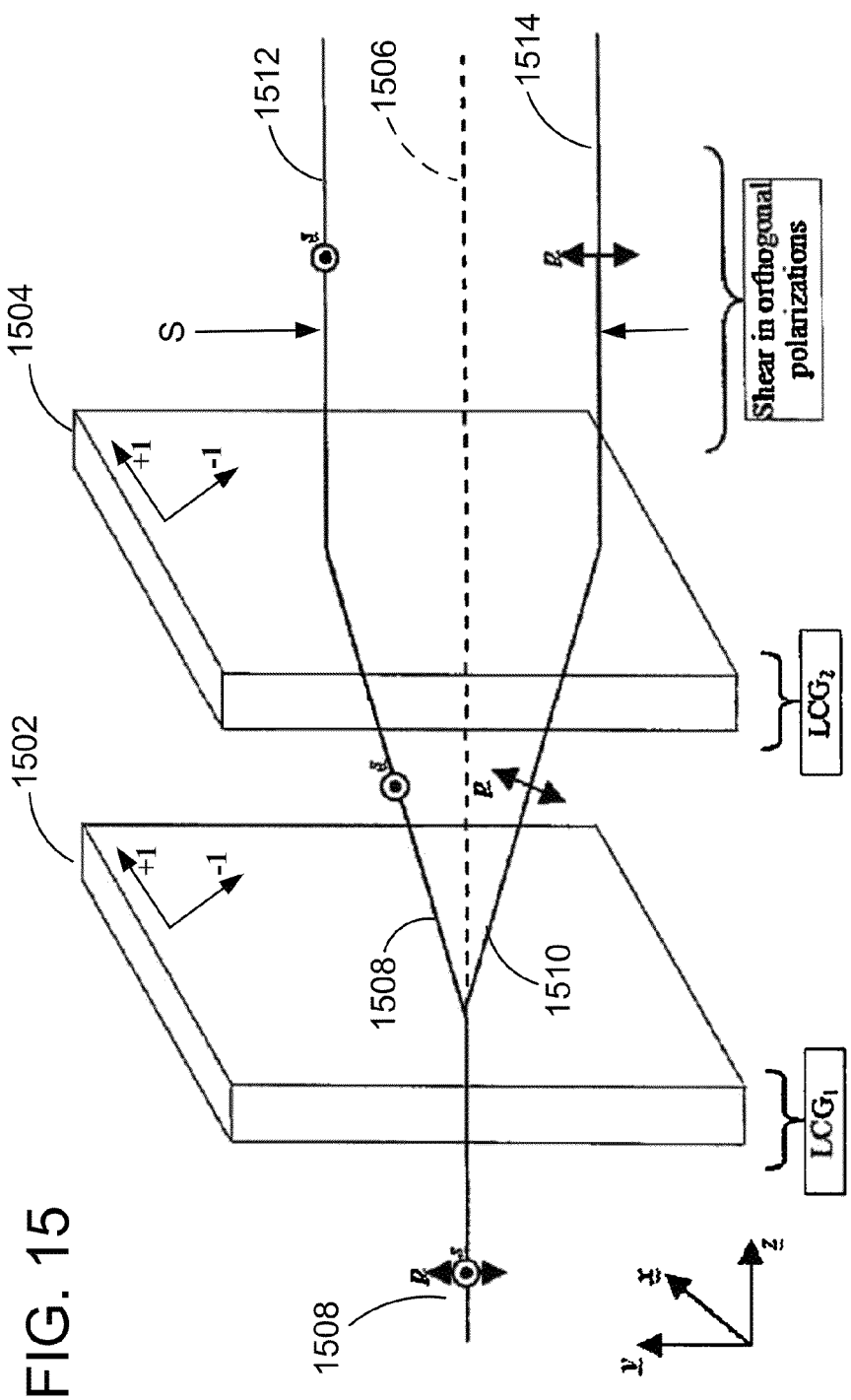
FIG. 15 illustrates production of a shear with polarizing liquid crystal gratings.

With reference to FIG. 15, a first liquid crystal grating (LCG1) 1502 and a second liquid crystal grating (LCG2)

1504 are situated on an axis 1506 so as to receive an input optical flux 1508 and produce a shear S between first and second polarization components. In the example of FIG. 15, the LCG 1502 diffracts an s-component upward into a +1 diffraction order along 1508 and a p-component downward into a −1 diffraction order along 1510. The LCG 1504 is also situated to diffract the s-component received from the LCG 1502 into a +1 diffraction order so as to exit the LCG 1504 along an axis 1512 that parallel to and displaced upwardly from the axis 1506. In addition, the LCG 1504 diffracts the received p-component into a −1 diffraction order along an axis 1514 that is parallel to and displaced downwardly from the axis 1506.

For convenience, FIG. 15 is described with reference to particular orthogonal linear polarizations, but any orthogonal polarization states can be similarly processed using one or more quarter waveplates, half waveplates, or other retardation plates, typically situated prior to the LCG 1502.

Example 13

Channeled Imaging Polarimeter Using PGs

Figure 16:
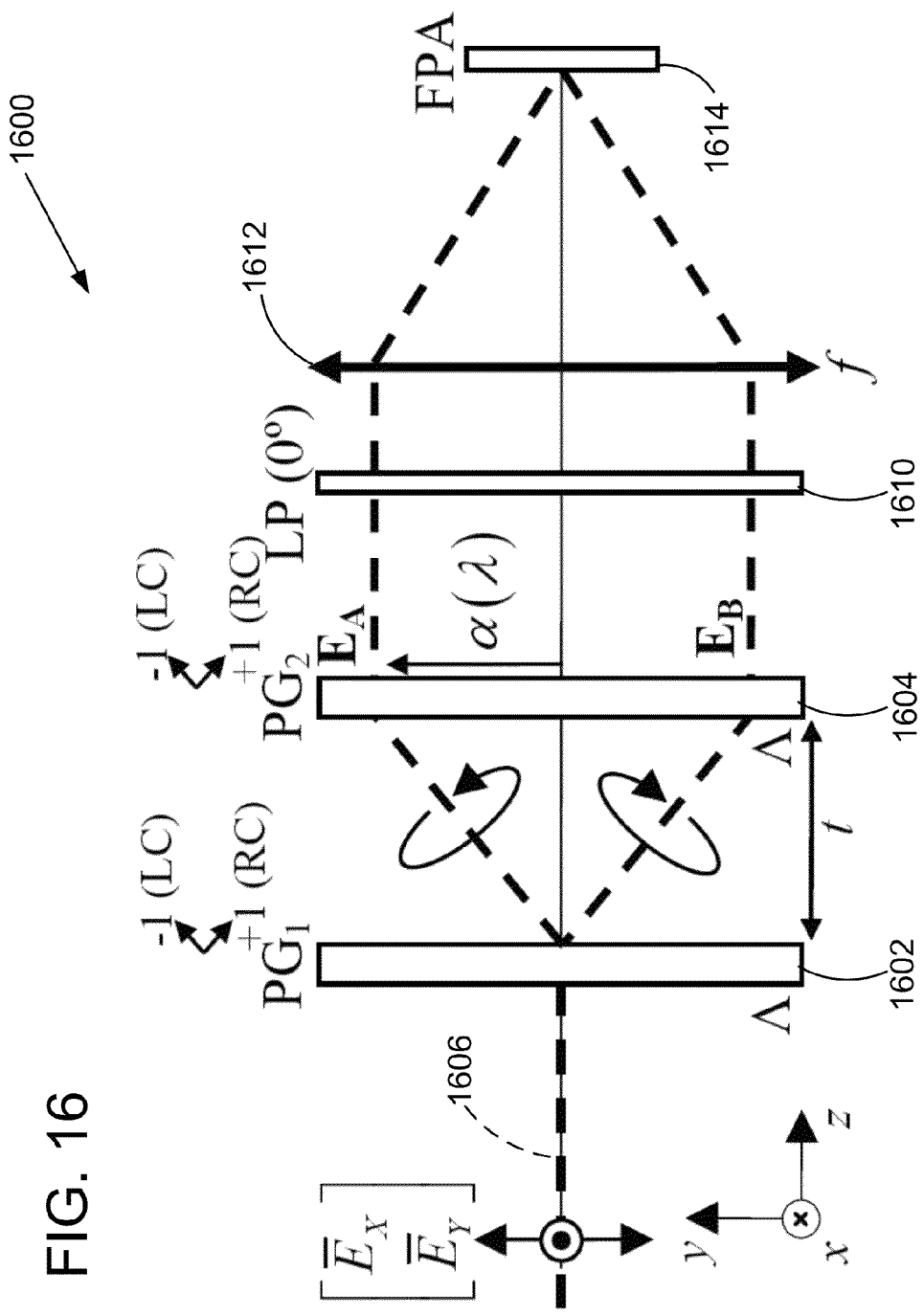
FIG. 16 is a schematic diagram of a CLI polarimeter using right circular (RC) and left circular (LC) polarizations diffracting into the −1 and +1 diffraction orders, respectively.

FIG. 16 illustrates a representative channeled imaging polarimeter (CIP) 1600. The CIP 1600 is configured to interferometrically generate carrier frequencies that are amplitude modulated based on spatially-dependent 2-dimensional Stokes parameters. Such a CIP exhibits inherent image registration and can be implemented with simple optical components. Image registration is inherent as all the Stokes parameters are directly modulated onto coincident interference fringes and the shear producing optical components can be added to nearly any pre-existing lens and camera system.

The CLI 1600 includes a first polarizing grating (PG) 1602 and a second PG 1604 that are situated along an axis 1606 and spaced apart by a distance t. The PGs 1602, 1604 provide shear similar to that produced by a diffractive Savart plate, so that interference fringes similar to a Sagnac interferometer's white-light fringes can be produced. Some or all Stokes parameters can be obtained. As shown in FIG. 16, the PGs 1602, 1604 have grating period Λ, and the PG 1604 is followed by a linear polarizer (LP) 1610 oriented with its transmission axis at 0° with respect to an X-axis axis. An objective lens 1612 with focal length fimages collimated light from the PGs 1602, 1604 to produce polarization modulated fringes at a focal plane array (FPA) 1614.

Various PGs can be used. In a convenient example, spatially-periodic birefringence devices are used based on liquid crystal (LC) materials such as described in Oh and Escuti, "Numerical analysis of polarization gratings using the finite-difference time-domain method," *Phys Rev A* 76 (4), 043815 (2007), Oh and Escuti, "Achromatic diffraction from polarization gratings with high efficiency," *Opt. Lett.* 33, 2287-2289 (2008), Crawford et al., "Liquid-crystal diffraction gratings using polarization holography alignment techniques," *J Appl Phys* 98, 123102 (2005), Escuti et al., "Simplified spectropolarimetry using reactive mesogen polarization gratings," *Proc. SPIE* 6302, 630207, (2006), Escuti et al., U.S. Patent Application Publication 2010/0110363, and Escuti et al., U.S. Patent Application Publication 2010/0225856, all of which are incorporated herein by reference.

Such PGs can serve as thin-film beamsplitters that are functionally analogous to Wollaston prisms. In both elements, incident light is angularly separated into two, forward-propagating, orthogonal polarizations. However, typical PGs are an embodiment of the Pancharatnam-Berry phase operating on circular eigen-polarizations, whereas Wollaston prisms are based on double refraction and operate on linear eigen-polarizations. Details of LC microstructure and holographic fabrication can be found in the references noted above.

The polarization behavior and diffraction efficiency spectra of such LC PGs are different than conventional phase or amplitude gratings. While the natural eigen-polarizations are circular (i.e., linearly proportional to $S_3/S_0$), LC PGs can be paired with a quarter waveplate (QWP) in order to separate incident light based on other desired polarizations (i.e., $S_1/S_0$ or $S_2/S_0$). Light diffracted from the PGs is directed almost entirely into the first (m=±1) or zero (m=0) diffraction orders, wherein diffraction angles are defined by the classical grating equation $\sin\theta_m = m\lambda/\Lambda - \sin\theta_{in}$, wherein Λ is the grating period, m is the grating order, and $\theta_m$ and $\theta_{in}$ are the diffracted and incidence angles, respectively. The diffraction efficiency of a PG can be typically expressed as:

$$\eta_{\pm 1} = \left(\frac{1}{2} \mp \frac{S_3}{2S_0}\right)K,$$

$$\eta_0 = (1 - K),$$

wherein K is a factor determined by the LC structure in the PG.

The CLI polarimeter 1600 preferably uses PGs that are capable of high efficiency operation over a broad (white-light) spectrum. The original LC-based PG had a relatively narrow diffraction efficiency spectrum such that high first-order efficiency (>99%) occurred only at wavelengths close to a specified design wavelength $\lambda_0$ (typically within $\Delta\lambda/\lambda_0 \sim 13\%$). However, broadband PGs having a high efficiency spectral bandwidth ($\Delta\lambda/\lambda_0 \sim 56\%$) which can cover most of the visible wavelength range are available. For these PGs, the factor K can be approximated as K=1, so that $\eta_{\pm 1}=1$ and $\eta_0=0$ for most visible wavelengths (e.g., 450-750 nm).

In the CLI polarimeter 1600, incident light is transmitted by $PG_1$ and diffracted into left and right circularly polarized components, propagating above and below the axis 1606, respectively. After transmission through $PG_2$, the two beams ($E_A$ and $E_B$) are diffracted again to propagate parallel to the optical axis 1606 and are now sheared by a distance 2α. The linear polarizer (LP) 1610 analyzes both beams, thus producing a common polarization state. Imaging both beams onto the FPA 1614 with the lens 1612 combines the two beams and produces interference fringes.

The intensity pattern on the FPA 1614 can be estimated by assuming that an arbitrarily polarized electric field is incident on the first polarization grating ($PG_1$). The incident field can be expressed as $$E_{inc} = \begin{bmatrix} \bar{E}_X \\ \bar{E}_Y \end{bmatrix} = \begin{bmatrix} E_X(\xi,\eta)e^{j\varphi_x(\xi,\eta)} \\ E_Y(\xi,\eta)e^{j\varphi_y(\xi,\eta)} \end{bmatrix},$$

wherein ξ, η are the angular spectrum components of x and y, respectively. The PG's +1 and −1 diffraction orders can be modeled as right and left circular polarization analyzers with their Jones matrices expressed as $$J_{+1,RC} = \frac{1}{2}\begin{bmatrix} 1 & i \\ -i & 1 \end{bmatrix},$$

-continued $$J_{-1,LC} = \frac{1}{2}\begin{bmatrix} 1 & -i \\ i & 1 \end{bmatrix}.$$

After transmission through $PG_1$ and $PG_2$, the x and y polarization components of the electric field, for each of the two beams, are $$E_A = J_{-1,LC}E_{inc} = \frac{1}{2}\begin{bmatrix} \bar{E}_X(\xi, \eta-\alpha) - j\bar{E}_Y(\xi, \eta-\alpha) \\ j\bar{E}_X(\xi, \eta-\alpha) + \bar{E}_Y(\xi, \eta-\alpha) \end{bmatrix},$$

$$E_B = J_{+1,RC}E_{inc} = \frac{1}{2}\begin{bmatrix} \bar{E}_X(\xi, \eta+\alpha) + j\bar{E}_Y(\xi, \eta+\alpha) \\ -j\bar{E}_X(\xi, \eta+\alpha) + \bar{E}_Y(\xi, \eta+\alpha) \end{bmatrix},$$

wherein α is the shear, calculated using the paraxial approximation as $$\alpha \cong \frac{m\lambda}{\Lambda}t$$

wherein m is a diffraction order (usually either 1 or −1). The total electric field incident on the linear polarizer (LP) 1610 is $$E_{LP}^+ = E_A + E_B = \frac{1}{2}\begin{bmatrix} \bar{E}_X(\xi, \eta+\alpha) + j\bar{E}_Y(\xi, \eta+\alpha) + \bar{E}_X(\xi, \eta-\alpha) - \\ j\bar{E}_Y(\xi, \eta-\alpha) - j\bar{E}_X(\xi, \eta+\alpha) + \bar{E}_Y(\xi, \eta+\alpha) + \\ j\bar{E}_X(\xi, \eta-\alpha) + \bar{E}_Y(\xi, \eta-\alpha) \end{bmatrix}.$$

Transmission through the linear polarizer, with its transmission axis at 0°, yields $$\bar{E}_{LP} = \begin{bmatrix} 1 & 0 \\ 0 & 0 \end{bmatrix} E_{LP}^+ =$$

$$\frac{1}{2}\begin{bmatrix} \bar{E}_X(\xi, \eta+\alpha) + j\bar{E}_Y(\xi, \eta+\alpha) + \bar{E}_X(\xi, \eta-\alpha) - j\bar{E}_Y(\xi, \eta-\alpha) \\ 0 \end{bmatrix}.$$

The objective lens 1614 produces a Fourier transformation of the field as, $$E_f = F[\bar{E}_{LP}]_{\xi=\frac{x}{\lambda f}, \eta=\frac{y}{\lambda f}} =$$

$$\frac{1}{2}\left[\bar{E}_X e^{j\frac{2\pi}{\lambda f}\alpha y} + j\bar{E}_Y e^{j\frac{2\pi}{\lambda f}\alpha y} + \bar{E}_X e^{-j\frac{2\pi}{\lambda f}\alpha y} - j\bar{E}_Y e^{-j\frac{2\pi}{\lambda f}\alpha y}\right],$$

wherein $\bar{E}_X$ and $\bar{E}_Y$ are now implicitly dependent upon x and y and f is the focal length of the objective lens 1614. Total electric field intensity can be written as follows:

$$I = |E_f|^2 = \frac{1}{2}(|\bar{E}_X|^2 + |\bar{E}_Y|^2) +$$

$$\frac{1}{4}(\bar{E}_X\bar{E}_X^* - \bar{E}_Y\bar{E}_Y^*)e^{j\frac{2\pi}{\lambda f}2\alpha y} + \frac{1}{4}(\bar{E}_X\bar{E}_X^* - \bar{E}_Y\bar{E}_Y^*)e^{-j\frac{2\pi}{\lambda f}2\alpha y} +$$

$$j\frac{1}{4}(\bar{E}_X\bar{E}_Y^* + \bar{E}_Y\bar{E}_X^*)e^{j\frac{2\pi}{\lambda f}2\alpha y} - j\frac{1}{4}(\bar{E}_X\bar{E}_Y^* + \bar{E}_Y\bar{E}_X^*)e^{-j\frac{2\pi}{\lambda f}2\alpha y}.$$

Simplification using the Stokes parameter definitions yields the final expression for the intensity pattern:

$$I(x, y) = \frac{1}{2}\left[S_0(x, y) + S_1(x, y)\cos\left(\frac{2\pi}{\lambda f}2\alpha y\right) + S_2(x, y)\sin\left(\frac{2\pi}{\lambda f}2\alpha y\right)\right]. \quad (20)$$

Consequently, the intensity recorded on the FPA 1614 contains the amplitude modulated Stokes parameters $S_0$, $S_1$ and $S_2$. Substitution of the shear into Eq. (20) produces an expression for intensity I:

$$I(x, y) = \frac{1}{2}\left[S_0(x, y) + S_1(x, y)\cos\left(2\pi\frac{2mt}{f\Lambda}y\right) + S_2(x, y)\sin\left(2\pi\frac{2mt}{f\Lambda}y\right)\right]. \quad (21)$$

From Eq. (2), the frequency of the interference fringes, or the carrier frequency, denoted by U is $$U = \frac{2mt}{f\Lambda}. \quad (22)$$

Thus, the linear Stokes parameters are amplitude modulated onto spectrally broadband (white-light) interference fringes.

Example 14

CLI Calibration

A CLI polarimeter such as that of FIG. 16 can be calibrated by applying a reference beam calibration technique as described in Oka and Saito, "Snapshot complete imaging polarimeter using Savart plates," Proc. SPIE 6295, 629508 (2006) and Kudenov et al., "Prismatic imaging polarimeter calibration for the infrared spectral region," *Opt. Exp.* 16, 13720-13737 (2008), both of which are incorporated herein by reference. First, a forward 2-dimensional (2D) Fourier transformation is performed on the intensity pattern of Eq. (21), producing $$I(\xi, \eta) = \quad (23)$$

$$F[I(x, y)] = \frac{1}{2}S_0(\xi, \eta) + \frac{1}{4}S_1(\xi, \eta) * [\delta(\xi, \eta+U) + \delta(\xi, \eta-U)] +$$

$$i\frac{1}{4}S_2(\xi, \eta) * [\delta(\xi, \eta+U) - \delta(\xi, \eta-U)],$$

wherein ξ and η are the Fourier transform variables for x and y, respectively, and ξ is the Dirac delta function. Eq. (23) indicates the presence of three "channels" in the Fourier domain. The $S_1$ and $S_2$ Stokes parameters are modulated (i.e., convolved) by two shifted (±U) delta functions, while the $S_0$ Stokes parameter remains unmodulated. These three channels are denoted as $C_0$ ($S_0$), $C_1$ (($S_1-iS_2$)δ(ξ,η−U)) and $C_1^*$ (($S_1+iS_2$)δ(ξ,η+U)), respectively. Applying a 2D filter to two of the three channels ($C_0$ and $C_1$ or $C_1^*$), followed by an inverse Fourier transformation, enables their content to be isolated from the other components. Inverse Fourier transformation of channels $C_0$ and $C_1$ produces $$C_0 = \frac{1}{2}S_0(x, y), \quad (24)$$

$$C_1 = \frac{1}{4}(S_1(x, y) - iS_2(x, y))e^{i2\pi Uy}. \quad (25)$$

Therefore, the $S_0$ Stokes parameter can be extracted directly from Eq. (24), while the $S_1$ and $S_2$ components are modulated by an exponential phase factor $e^{i2\pi Uy}$. Isolating this phase factor from the sample data ($C_{0,sample}$ and $C_{1,sample}$) is accomplished by comparing it to a previously measured reference polarization state ($C_{0,ref}$ and $C_{1,ref}$) containing the known distribution $[S_{0,ref}, S_{1,ref}, S_{2,ref}, S_{3,ref}]^T$. The sample's Stokes parameters are demodulated by dividing the sample data by the reference data, followed by normalization to the $S_0$ Stokes parameter and extraction of the real and imaginary parts, $$S_0(x, y) = |C_{0,sample}|, \quad (26)$$

$$\frac{S_1(x, y)}{S_0(x, y)} = \Re\left[\frac{C_{1,sample}}{C_{1,reference}} \frac{C_{0,reference}}{C_{0,sample}}\left(\frac{S_{1,ref}(x, y) - iS_{3,ref}(x, y)}{S_{0,ref}(x, y)}\right)\right], \quad (27)$$

$$\frac{S_2(x, y)}{S_0(x, y)} = \Im\left[\frac{C_{1,sample}}{C_{1,reference}} \frac{C_{0,reference}}{C_{0,sample}}\left(\frac{S_{1,ref}(x, y) - iS_{2,ref}(x, y)}{S_{0,ref}(x, y)}\right)\right]. \quad (28)$$

For instance, using reference data created by a linear polarizer, oriented at 0° $[S_0, S_1, S_2, S_3]^T = [1, 1, 0, 0]^T$, yields the following reference-beam calibration equations:

$$S_0(x, y) = |C_{0,sample}|, \quad (29)$$

$$\frac{S_1(x, y)}{S_0(x, y)} = \Re\left[\frac{C_{1,sample}}{C_{1,reference}} \frac{C_{0,reference}}{C_{0,sample}}\right], \quad (30)$$

$$\frac{S_2(x, y)}{S_0(x, y)} = \Im\left[\frac{C_{1,sample}}{C_{1,reference}} \frac{C_{0,reference}}{C_{0,sample}}\right]. \quad (31)$$

Eqns. (29)-(31) are applied to the measured data in order to extract the scene's spatially-dependent Stokes parameters.

Example 15

CLI Polarimeter Implementation

Figure 17:
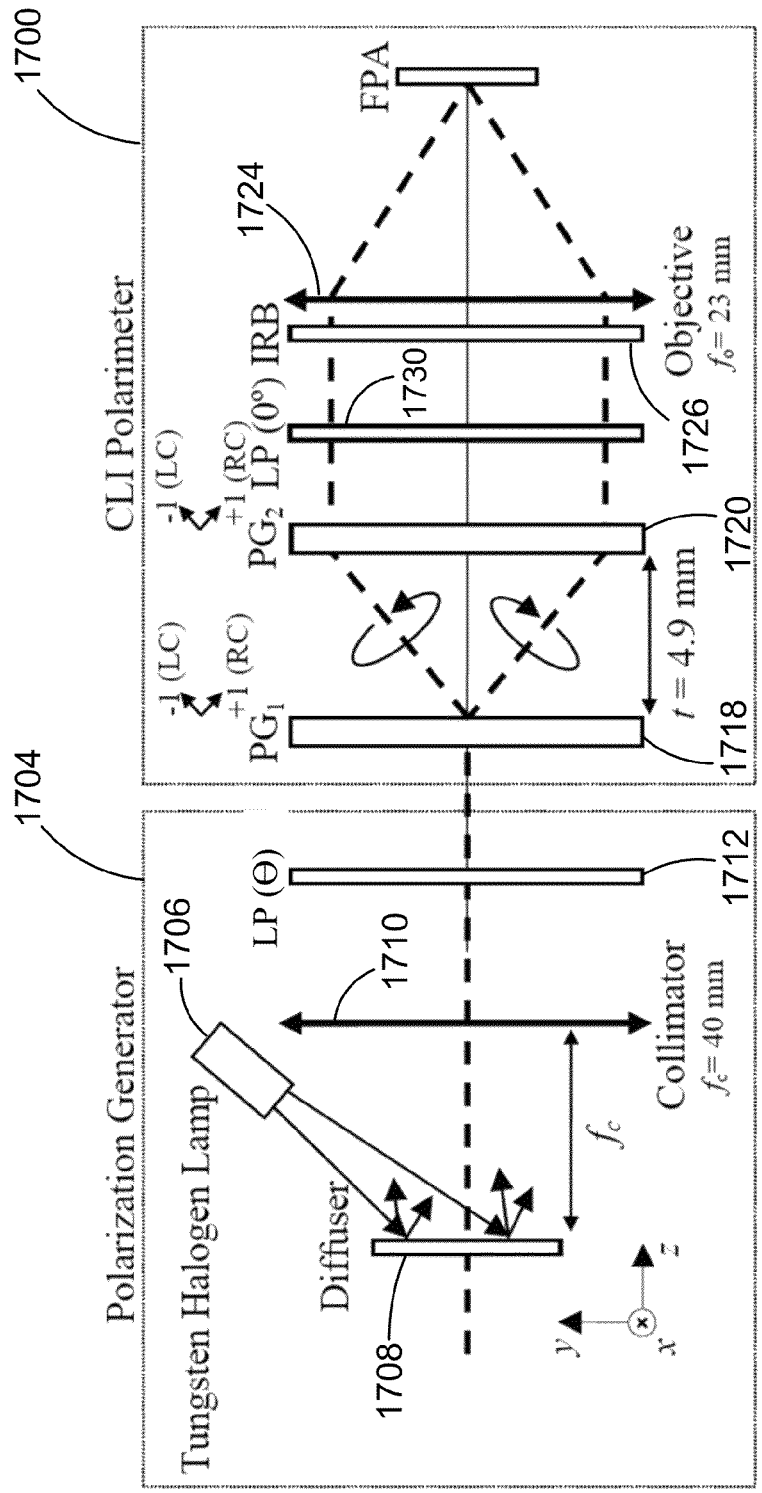
FIG. 17 is an arrangement for establishing the measurement accuracy of a CLI polarimeter in white-light.

An experimental configuration for establishing the measurement accuracy of a CLI polarimeter 1700 in white-light is illustrated in FIG. 17. A linear polarization generator (LPG) 1704 includes a tungsten halogen fiber-lamp 1706 configured to illuminate a diffuse white ceramic plate 1708. The diffuser 1708 is positioned near the focal point of a collimating lens 1710 with an effective focal length, $f_c$, of 40 mm. Collimated light propagates to a linear polarizer 1712 oriented with its transmission axis at θ. The polarization generator 1704 produces a uniformly polarized scene for the CLI polarimeter 1700 to image. The period of polarization gratings ($PG_1$ and $PG_2$) 1718, 1720 is Λ=7.9 m and the focal length of an objective lens 1724 is $f_o$=23 mm. An infrared blocking filter (IRB) 1726 is situated in front of the objective lens 1724 to limit the spectral passband of the imaged light to 410-750 nm. Lastly, a FPA 1730 is an 8-bit monochrome machine vision camera, containing 640×480 pixels, placed at the focal point of the objective lens 1724. A linear polarizer 1730 is configured to analyze the sheared beams.

Example 16

Calibration Verification

Figure 18A:
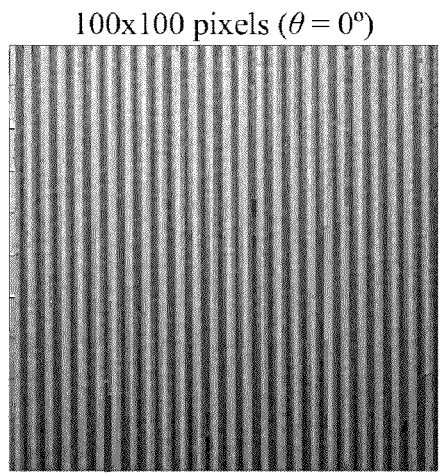
FIGS. 18A-18C are white-light interference fringe patterns generated in a central 100×100 pixels on a focal plane array at polarizer orientations of θ=0°, θ=50°, and θ=90°, respectively.
Figure 18B:
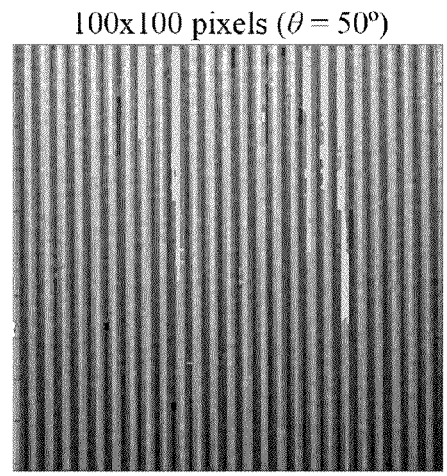
Figure 18C:
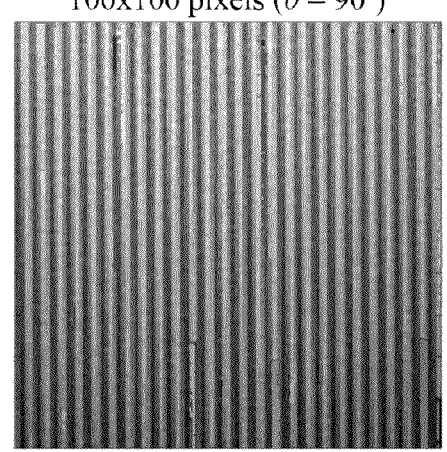

In order to verify the mathematical relationship of Eq. (2), in addition to the calibration accuracy defined at a constant illumination condition, reference data were taken with the apparatus of FIG. 17 and rotating the LP 1712 for angles θ between 0° and 180° in 10° increments. After reconstruction, a central portion of the field of view (FOV) was averaged over a 100×100 pixel area to obtain an average value for the measured polarization state. Images of the white-light interference fringes from this 100×100 pixel area are depicted in FIGS. 18A-18C for θ equal to 0°, 50° and 90°, respectively.

Figure 19:
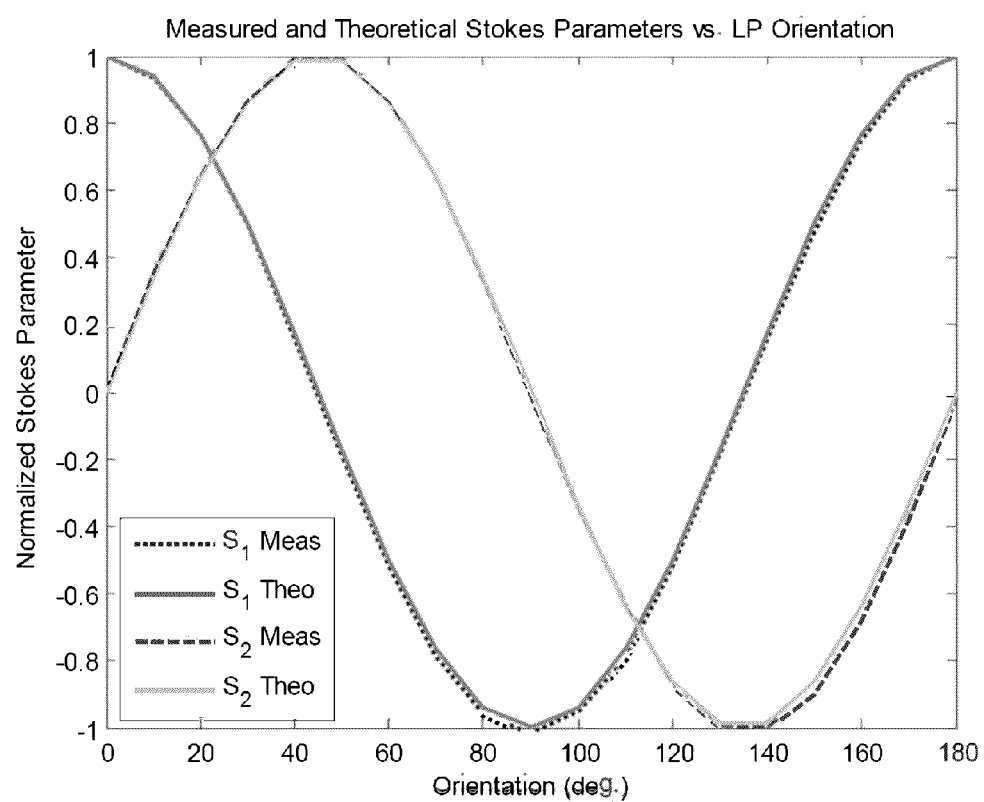
FIG. 19 is a graph comparing measured and theoretical polarimetric reconstructions.

Note that the phase of the sinusoidal fringes changes while the amplitude remains constant for varying linear polarizer orientations. This phase change is directly related to Eq. (21), and indicates the varying proportions of $S_1$ to $S_2$ as the LP 1712 is rotated. Meanwhile, the amplitude remains constant because the degree of linear polarization (DOLP= $\sqrt{S_1^2+S_2^2}/S_0$) from the LPG 1704 is constant (~1). Plotting the measured $S_1$ and $S_2$ Stokes parameters versus θ and comparing them to the theoretical values yields the results depicted in FIG. 19. The calculated RMS error for both curves is approximately 1.6%. This implies that the amplitude modulation of Eq. (21) accurately follows the incident Stokes parameter variation.

Example 17

Polarization Grating Performance

Figure 20:
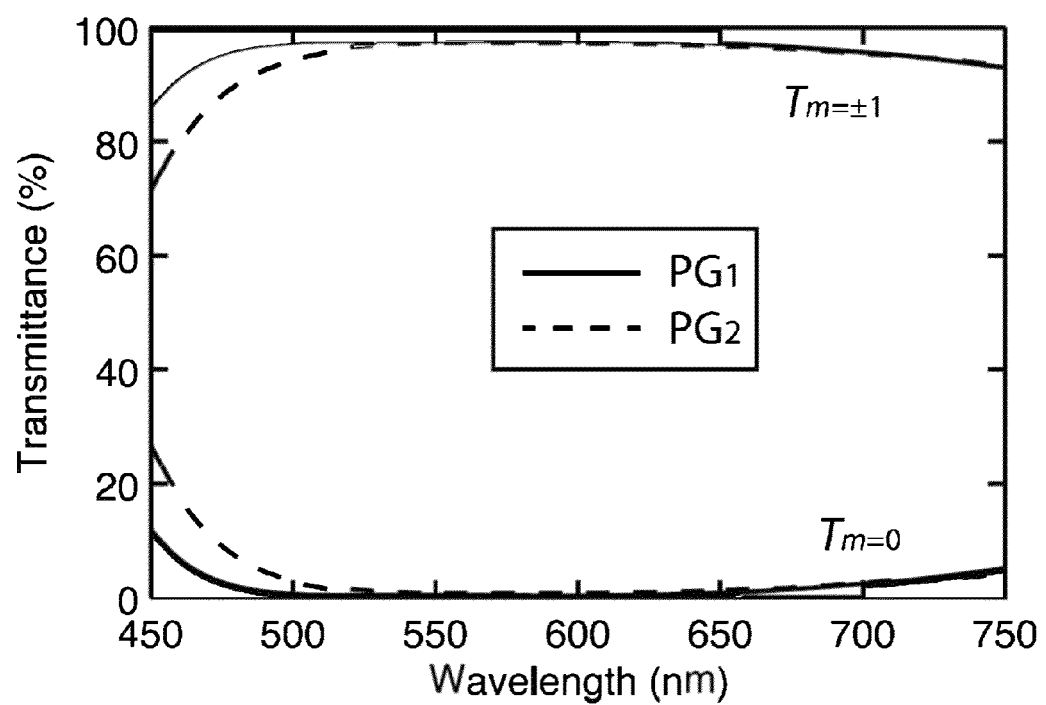
FIG. 20 includes measured zero-order and total first-order ($T_{\pm 1}=T_{+1}+T_{-1}$) transmission spectra of a representative polarization grating.

To assess the performance of PGs, zeroth diffraction order transmissions can be measured. This provides an approximate metric for how efficiently PGs diffract light into the +/−1 diffraction orders. Results of typical transmission measurements are shown in FIG. 20, demonstrating that the PGs are highly efficient for wavelengths spanning 500-750 nm, but rather inefficient below 475 nm. Consequently, zero-order light transmitted at wavelengths less than 475 nm can cause error in the calculated Stokes parameters, primarily in the normalization of the measured Stokes parameters to $S_0$. Expressing the Stokes parameters in Eq. (21) as spectrally band-integrated functions yields $$S'_n(x, y) = \int_{\lambda_1}^{\lambda_2} DE^2(\lambda) S_n(x, y, \lambda) d\lambda,$$

wherein DE is the diffraction efficiency of one PG for the +1st or −1st order, the prime superscript on the Stokes parameters indicate that they have been spectrally band-integrated, and the subscript n=0, 1, or 2 indicates the $S_0$, $S_1$, or $S_2$ Stokes parameter, respectively. It is assumed for this example that both PGs have the same DE as a function of wavelength. In a spectral region where the DE is not ideal, such that DE<1.0, then some light transmitted through the PGs is not diffracted. This can be introduced to the model [Eq. (21)] as an additional unmodulated zero-order undiffracted offset term $\Delta_{offset}$:

$$I(x, y) = \frac{1}{2}\left[\Delta_{offset}(x, y) + S'_0(x, y) + S'_1(x, y)\cos\left(2\pi\frac{2mt}{f\Lambda}y\right) + S'_2(x, y)\sin\left(2\pi\frac{2mt}{f\Lambda}y\right)\right],$$

Reconstructing via Eqns. (26)-(28) yields the appropriate absolute results for $S_1$ and $S_2$; however, $S_0$ will be erroneous due to the additional offset. Therefore, measured normalized Stokes parameters can be introduced and denoted by double primes $$S_0''(x, y) = S_0'(x, y) + \Delta_{offset}(x, y),$$

$$\frac{S_n''(x, y)}{S_0''(x, y)} = \frac{S_n'(x, y)}{S_0'(x, y) + \Delta_{offset}(x, y)},$$

wherein the subscript n=1 or 2 indicates the $S_1$ or $S_2$ Stokes parameter, respectively. Consequently, error is induced into the $S_1$ and $S_2$ Stokes parameters from the normalization to the effectively larger $S_0$ component ($S_0'((x, y)+\Delta_{offset}(x, y))$. While error due to this zero-order light leakage was observed in some outdoor tests, it was negligible in laboratory characterizations in which an $S_0$ reference and sample illumination levels were constant. PG's with a zero-order light transmission less than 3% over the passband would enable better accuracy regardless of the $S_0$ illumination level.

Example 18

Outdoor Measurements

The snapshot imaging capability of a CLI polarimeter was also assessed outdoors on moving targets. For outdoor scenes, the absolute accuracy of the Stokes parameters for varying illumination levels is not well established, again due to the zero-order diffraction efficiency leakage discussed previously. Outdoor results are provided here to demonstrate snapshot imaging and reconstruction capabilities in full sunlight.

Figure 21:
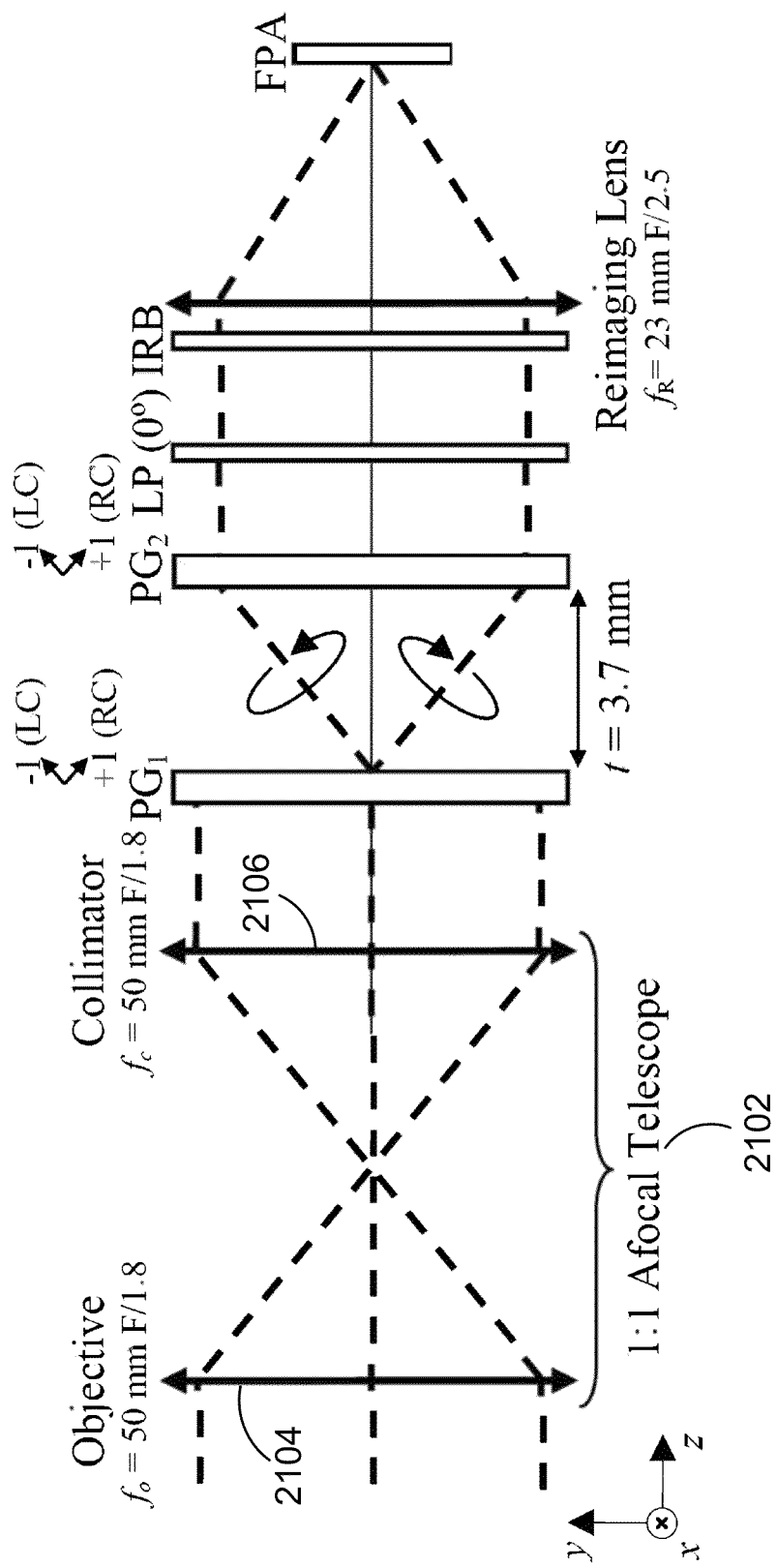
FIG. 21 is a schematic diagram of an experimental setup for viewing outdoor targets with a CLI polarimeter. An afocal telescope is included to allow the scene to be defocused while maintaining focus on the interference fringes.
Figure 22:
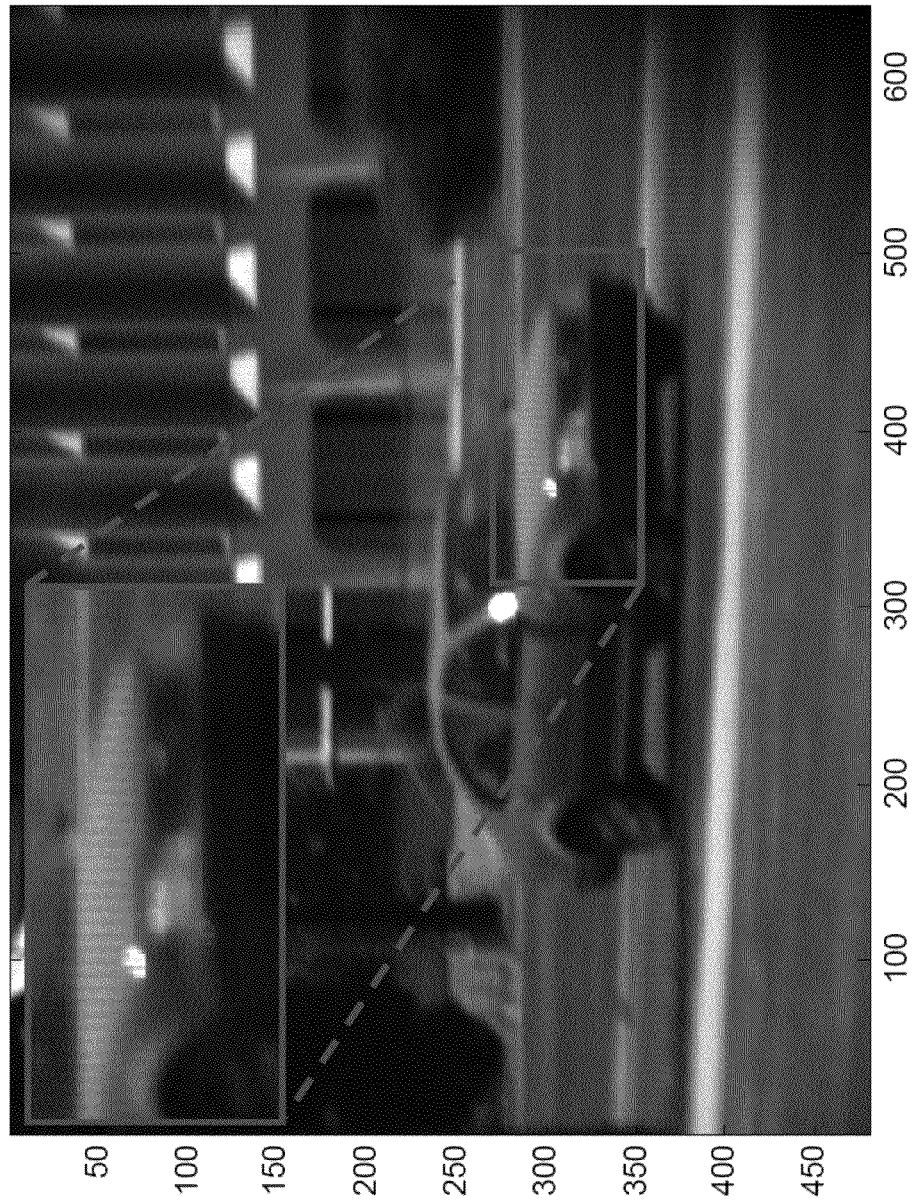
FIG. 22 is a raw image of a moving vehicle prior to extraction of Stokes parameters. Interference fringes are located in areas of the scene that are linearly polarized and are particularly evident in the vehicle hood.
Figure 23A:
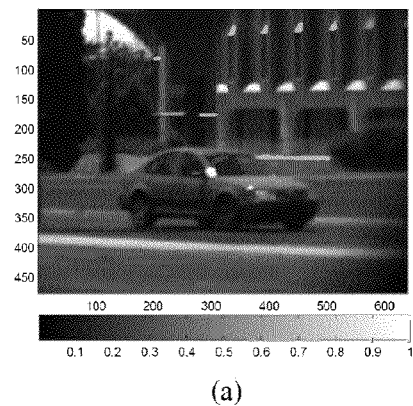
FIGS. 23A-23D are images obtained from the polarization data corresponding to the image of FIG. 22, wherein the images are based on $S_0$, degree of linear polarization (DOLP), $S_1/S_0$ and $S_2/S_0$, respectively.
Figure 23B:
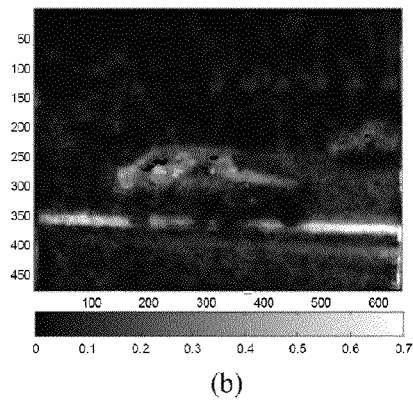
Figure 23C:
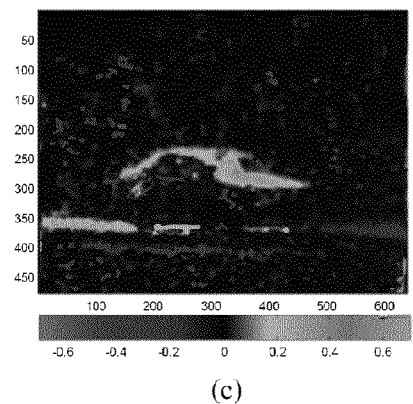
Figure 23D:
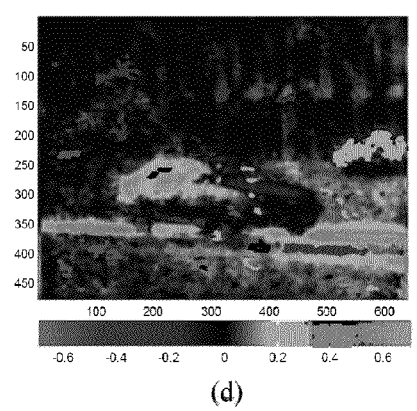

The optical configuration for these tests is depicted in FIG. 21. A 1:1 afocal telescope 2102 includes two 50 mm focal length lenses 2104, 2106 operating at a focal number of F/1.8. These optics enable defocus to be introduced into a scene image while simultaneously maintaining focus on the fringes that are localized at infinity. Defocus is used to band-limit the spatial frequency content of the scene, thereby reducing aliasing artifacts in the reconstructed Stokes parameters. A raw image of a moving vehicle, captured with the CLI polarimeter, is depicted in FIG. 22. The image was taken on a clear and sunny afternoon with an exposure time of approximately 1/1200 second with a re-imaging lens focal number of F/2.5. Reference data, taken of a linear polarizer oriented at 0° in front of a diffuser, was measured shortly after the vehicle was imaged. The diffuser was illuminated by sunlight.

The polarization data was extracted by taking a fast Fourier transformation of the raw data, followed by filtration, an inverse Fourier transformation, and calibration by application of Eqns. (26)-(28). The reconstructed data were also processed with an aliasing reduction filter that reduces noise due to aliasing artifacts. This produced the data depicted in FIG. 23A-23D corresponding to $S_0$, degree of linear polarization (DOLP), $S_1/S_0$, and $S_2/S_0$, respectively, wherein $$DOLP(x, y) = \frac{\sqrt{S_1^2(x, y) + S_2^2(x, y)}}{S_0(x, y)}.$$

The orientation of the linearly polarized light ($\theta_L$) can be extracted from the measured Stokes parameters using the formula $$\theta_L(x, y) = \frac{1}{2}\tan^{-1}\left(\frac{S_2(x, y)}{S_1(x, y)}\right). \tag{32}$$

By incorporating a color fusion method, this orientation information can be superimposed onto the DOLP and intensity ($S_0$) information. In color fusion, a hue (pixel color), saturation (amount of color within the pixel) and value (pixel brightness) color-mapping is used. This Hue-Saturation-Value (HSV) color map is mapped directly into linear polarization orientation (hue), DOLP (saturation), and intensity $S_0$ (value). Images generated with this scheme provide a qualitative assessment of polarimetric and intensity information. A color fusion image can be generated from the image data associated with FIGS. 23A-23D, along with orientation information calculated from Eq. (32) above.

Example 19

Full Stokes Polarimetry

Figure 24A:
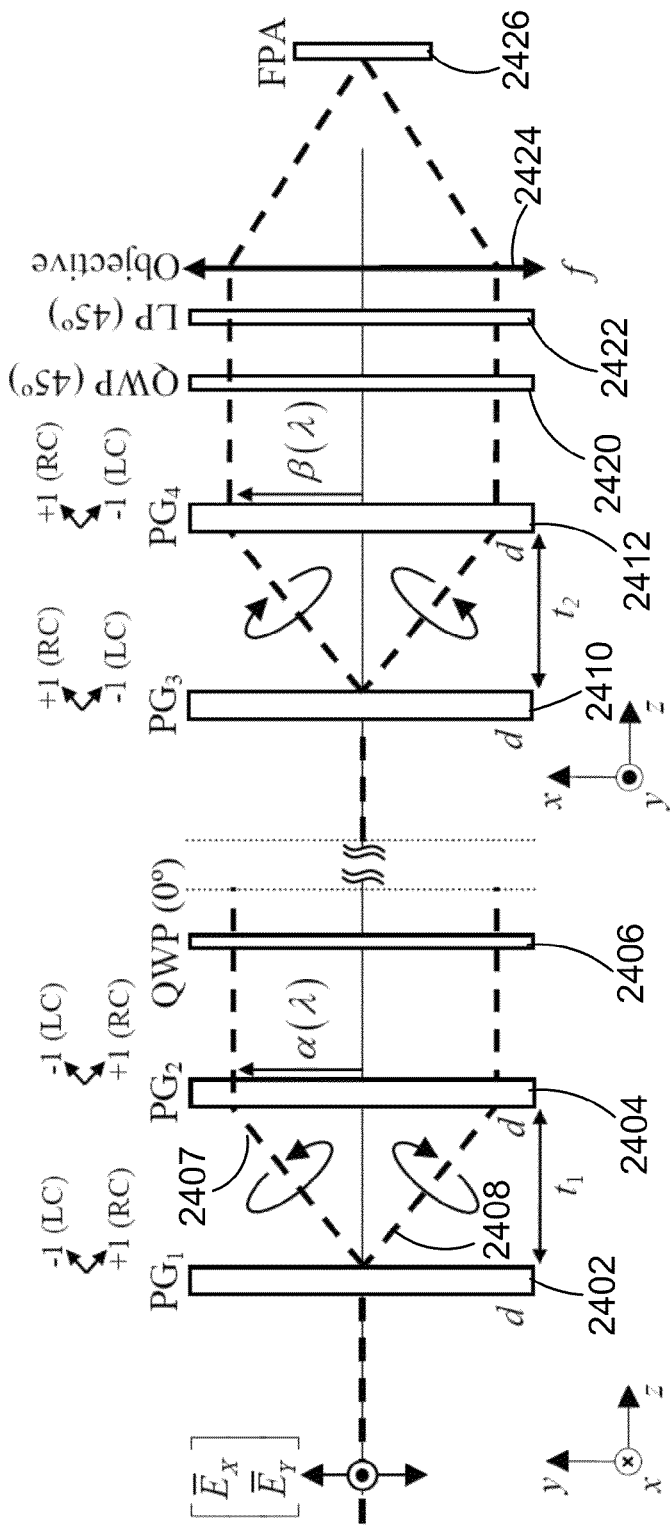
FIG. 24A is a schematic of a full imaging Stokes polarimeter that can provide images based on all four Stokes parameters. Polarization gratings $PG_1$ and $PG_2$ diffract in the yz plane, while polarization gratings $PG_3$ and $PG_4$ diffract in the xz plane.

A CLI polarimeter can be analyzed as a subset of a Savart-plate Stokes imaging polarimeter. By replacing each Savart plate with two PGs, a white-light Stokes imaging polarimeter capable of measuring $S_0$, $S_1$, $S_2$ and $S_3$ can be realized. An optical layout for this scheme is depicted schematically in FIG. 24A-24B. Light transmitted by $PG_1$ 2402 and $PG_2$ 2404 is sheared along a y axis by a distance $\alpha$ to produce two circularly polarized diffracted beams 2407, 2408 that are converted into linearly polarized light after propagation through a quarter wave plate (QWP) 2406. Transmission through $PG_3$ 2410 and $PG_4$ 2412 shears each of the beams 2407, 2408 along the x axis by a distance $\beta$. Propagation of the four circularly polarized beams through a QWP 2420, linear polarizer 2422, and objective lens 2424 generates white-light polarization interference fringes at an FPA 2426. Propagation of a single polarized ray is depicted in the perspective view in FIG. 24B.

For the purposes of the following derivation, the $PG_1$ to $PG_2$ separation ($t_1$) is equal to the $PG_3$ to $PG_4$ separation ($t_2$), such that $t_1=t_2=t$. Furthermore, all four PGs have an identical grating period $\Lambda$. The incident arbitrarily polarized electric field is defined as $$E_{inc} = \begin{bmatrix} \overline{E}_X \\ \overline{E}_Y \end{bmatrix} = \begin{bmatrix} E_X(\xi, \eta)e^{j\varphi_x(\xi,\eta)} \\ E_Y(\xi, \eta)e^{j\varphi_y(\xi,\eta)} \end{bmatrix}.$$

After transmission through $PG_1$ and $PG_2$, the x and y components of the electric field for $E_A$ and $E_B$ are identical to those of Example 13 above. Propagation through the QWP 2420, oriented with its fast-axis at 0°, yields $$E_A' = \begin{bmatrix} 1 & 0 \\ 0 & -j \end{bmatrix} E_A = \frac{1}{2}\begin{bmatrix} \overline{E}_X(\xi, \eta-\alpha) - j\overline{E}_Y(\xi, \eta-\alpha) \\ \overline{E}_X(\xi, \eta-\alpha) - j\overline{E}_Y(\xi, \eta-\alpha) \end{bmatrix},$$

$$E_B' = \begin{bmatrix} 1 & 0 \\ 0 & -j \end{bmatrix} E_B = \frac{1}{2}\begin{bmatrix} \overline{E}_X(\xi, \eta+\alpha) + j\overline{E}_Y(\xi, \eta+\alpha) \\ -\overline{E}_X(\xi, \eta+\alpha) - j\overline{E}_Y(\xi, \eta+\alpha) \end{bmatrix}.$$

Figure 24B:
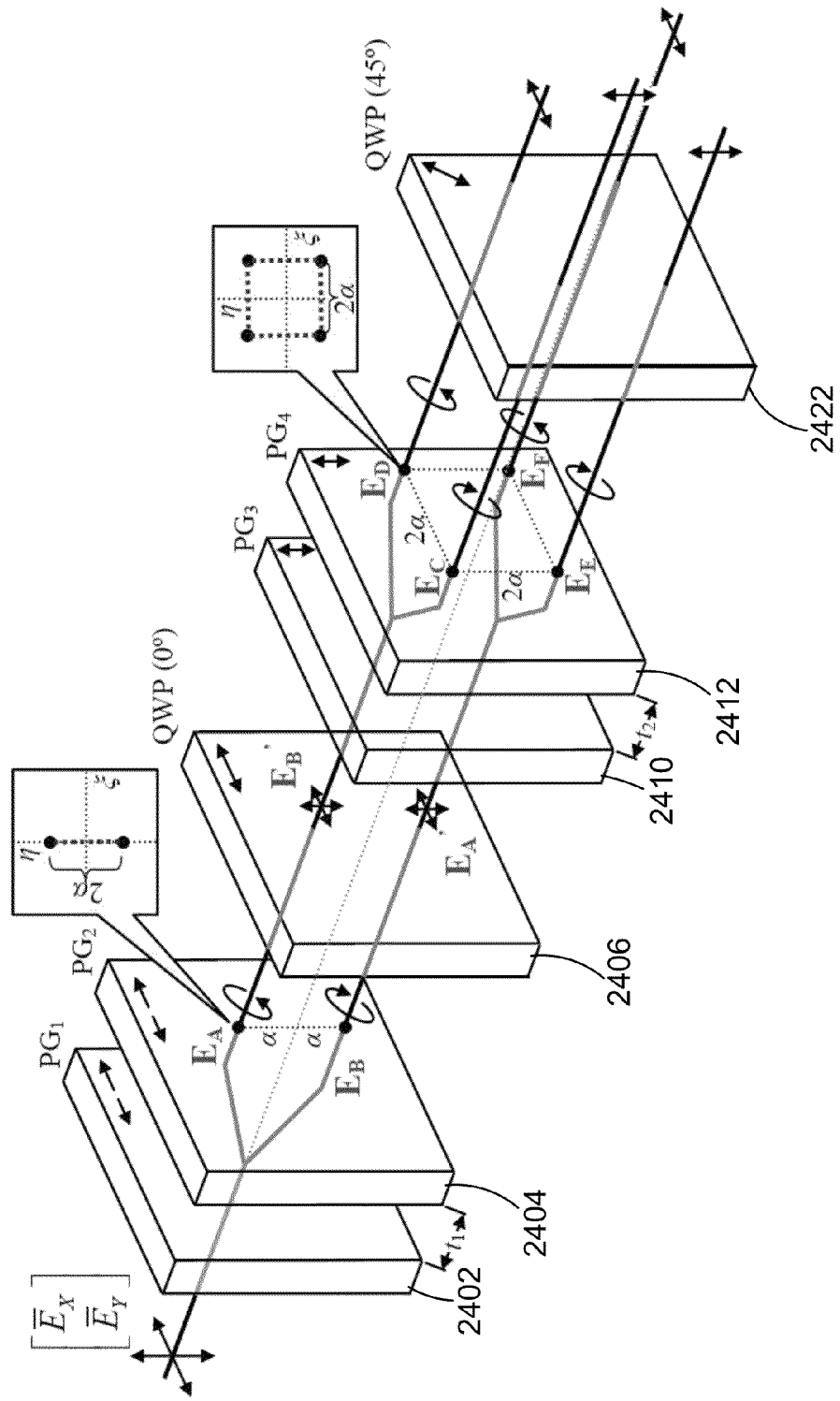
FIG. 24B is a perspective view of the polarimeter of FIG. 24A.

Propagation of $E_A'$ and $E_B'$ through $PG_3$ and $PG_4$ yields 4 beams, labeled $E_C$, $E_D$, $E_E$ and $E_F$ in FIG. 24B. These four transmitted fields are expressed by $$E_C(\xi+\alpha, \eta-\alpha) = J_{-1,LC}E'_A(\xi, \eta-\alpha) = \frac{1}{4}\begin{bmatrix}(\overline{E}_X - \overline{E}_Y) - j(\overline{E}_X + \overline{E}_Y) \\ (\overline{E}_X + \overline{E}_Y) + j(\overline{E}_X - \overline{E}_Y)\end{bmatrix},$$

$$E_D(\xi-\alpha, \eta-\alpha) = J_{+1,RC}E'_A(\xi, \eta-\alpha) = \frac{1}{4}\begin{bmatrix}(\overline{E}_X + \overline{E}_Y) + j(\overline{E}_X - \overline{E}_Y) \\ (\overline{E}_X - \overline{E}_Y) - j(\overline{E}_X + \overline{E}_Y)\end{bmatrix},$$

$$E_E(\xi+\alpha, \eta+\alpha) = J_{-1,LC}E'_B(\xi, \eta+\alpha) = \frac{1}{4}\begin{bmatrix}(\overline{E}_X - \overline{E}_Y) + j(\overline{E}_X + \overline{E}_Y) \\ -(\overline{E}_X + \overline{E}_Y) + j(\overline{E}_X - \overline{E}_Y)\end{bmatrix},$$

$$E_F(\xi-\alpha, \eta+\alpha) = J_{+1,RC}E'_B(\xi, \eta+\alpha) = \frac{1}{4}\begin{bmatrix}(\overline{E}_X + \overline{E}_Y) - j(\overline{E}_X - \overline{E}_Y) \\ -(\overline{E}_X - \overline{E}_Y) - j(\overline{E}_X + \overline{E}_Y)\end{bmatrix},$$

where $\overline{E}_X$ and $\overline{E}_Y$ are implicitly dependent on $\xi$, $\eta$, and $\alpha$. Transmission through the last QWP 2420, with its fast-axis oriented at 45°, rotates the circular polarization states of $E_C$, $E_D$, $E_E$ and $E_F$ into vertical and horizontal linear polarizations. Propagation of these beams through the analyzing linear polarizer 2422 unifies them into a 45° linear polarization state. The complete x and y components of the electric field incident on the lens 2424 are:

$$E^L_X = E^L_Y = \frac{1}{4}(\overline{E}_X(\xi+\alpha, \eta-\alpha) - j\overline{E}_Y(\xi+\alpha, \eta-\alpha)) +$$
$$(\overline{E}_X(\xi-\alpha, \eta-\alpha) - j\overline{E}_Y(\xi-\alpha, \eta-\alpha)) +$$
$$(j\overline{E}_X(\xi+\alpha, \eta+\alpha) - \overline{E}_Y(\xi+\alpha, \eta+\alpha)) +$$
$$(-j\overline{E}_X(\xi-\alpha, \eta+\alpha) + \overline{E}_Y(\xi-\alpha, \eta+\alpha)).$$

The lens 2424 produces a Fourier transformation of the field. Performing this on the $E^L_X$ component yields $$E_L =$$

$$F[E^L_X]_{\xi=\frac{x}{\lambda f}, \eta=\frac{y}{\lambda f}} = \frac{1}{4}(\overline{E}_X - j\overline{E}_Y)e^{j\frac{2\pi}{\lambda f}\alpha(x-y)} + (-j\overline{E}_X + \overline{E}_Y)e^{-j\frac{2\pi}{\lambda f}\alpha(x-y)} +$$
$$(j\overline{E}_X - \overline{E}_Y)e^{j\frac{2\pi}{\lambda f}\alpha(x+y)} + (\overline{E}_X - j\overline{E}_Y)e^{-j\frac{2\pi}{\lambda f}\alpha(x+y)},$$

wherein $\overline{E}_X$ and $\overline{E}_Y$ are implicitly dependent on x and y, f is the focal length of the objective lens 2424, and $\lambda$ is the wavelength of the incident illumination. The intensity is calculated by taking the absolute value squared of $E_L$. Simplifying the expression with the Stokes parameter definitions, combining terms into cosines and sines, and substituting the shear $\alpha$ from:

$$\alpha \cong \frac{m\lambda}{\Lambda}t,$$

produces the final intensity pattern on the FPA 2426:

$$I(x, y) = \frac{1}{2}S_0(x, y) + \frac{1}{2}S_3(x, y)\cos\left(2\pi\frac{2mt}{f\Lambda}x\right) +$$
$$\frac{1}{4}S_2(x, y)\left[\cos\left(2\pi\frac{2mt}{f\Lambda}(x-y)\right) - \cos\left(2\pi\frac{2mt}{f\Lambda}(x+y)\right)\right] +$$
$$\frac{1}{4}S_1(x, y)\left[\sin\left(2\pi\frac{2mt}{f\Lambda}(x-y)\right) + \sin\left(2\pi\frac{2mt}{f\Lambda}(x+y)\right)\right].$$

This configuration enables the measurement of all four Stokes parameters by isolating the various white-light spatial carrier frequencies $U_1$ and $U_2$, defined as $$U_1 = 2\frac{mt}{f\Lambda},$$

$$U_2 = 2\sqrt{2}\frac{mt}{f\Lambda}.$$

Additional Examples

The examples above are representative only and are selected for purposes of illustration. In other examples, the same or different combinations of polarization parameters such as Stokes parameters can be estimated, and interferometers that include additional reflective surfaces and/or polarization diffraction gratings can be used. Some examples are described with respect to linear polarizers, but in other examples, circular polarizers can be used. In view of the many possible embodiments to which the principles of the disclosed technology may be applied, it should be recognized that the illustrated embodiments are only preferred examples and should not be taken as limiting. I claim as my invention all that comes within the scope and spirit of the appended claims.

I claim:

1. An apparatus, comprising:
   at least two polarizing gratings that produce a dispersion compensated shear between portions of the an input light flux associated with first and second polarizations;
   a detector situated to receive an output light flux corresponding to a combination of the sheared first and second portions of the input light flux and produce an image signal;
   a polarization analyzer situated between the at least one grating and the detector; and
   an image processor that produces a polarization image based on the image signal, wherein the at least two polarizing gratings includes a first grating situated to produce a first shear portion by directing the first polarization along a first direction and the second polarization along a second direction, and a second grating situated to produce a second shear portion by directing the first polarization directed by the first grating along the second direction and the second polarization directed by the first grating along the first direction.

2. The apparatus of claim 1, wherein the first polarization and the second polarizations are orthogonal linear polarizations or left and right circular polarizations.

3. The apparatus of claim 1, wherein the at least one polarizing grating includes a first pair and a second pair of polarizing gratings configured to produce dispersion compensated shear along a first axis and a second axis.

4. The apparatus of claim 1, wherein the detector is an array detector.

5. The apparatus of claim 4, wherein the image processor is configured to produce the polarization image based on an amplitude modulation of interference fringes.

6. The apparatus of claim 5, wherein the image processor is configured to select at least one spatial frequency component of the recorded image signal and determine an image polarization characteristic based an intensity modulation associated with an image signal variation at the selected spatial frequency.

7. The apparatus of claim 6, wherein the image polarization characteristic is one or more or a combination of Stokes parameters $S_0$, $S_1$, $S_2$, and $S_3$.

8. The apparatus of claim 1, wherein the polarizing gratings are blazed birefringent gratings.

9. The apparatus of claim 1, wherein the polarizing gratings are liquid crystal gratings.

10. The apparatus of claim 1, wherein the dispersion compensated shear is proportional to a separation between the first grating and the second grating.

11. The apparatus of claim 1, wherein the first grating is situated to direct the first polarization above and away from the optical axis and the second polarization below and away from the optical axis, and the second grating is configured to direct the first polarization and the second polarization back towards the optical axis so as to produce the dispersion compensated shear.

12. The apparatus of claim 1, wherein the first grating and the second grating have identical grating periods.

13. The apparatus of claim 1, wherein the polarization image is a two dimensional image.

14. The apparatus of claim 1, wherein shear for a spectral component of the input optical flux is proportional to a wavelength associated with the spectral component.

15. A method, comprising:
receiving an input optical flux;
producing a shear between first and second portions of the input optical flux associated with first and second states of polarization that is proportional to a wavelength of the input optical flux by directing the first and second portions to a pair of polarizing gratings; and
estimating a polarization characteristic of the input optical flux based on a spatial frequency associated with the shear in an intensity pattern obtained by combining the sheared first and second portions of the input optical flux.

16. The method of claim 15, further comprising diffracting each of the first and second portions of the incident optical flux at the at least one diffraction grating so as to produce a shear having a magnitude associated with a grating period and a wavelength associated with the input optical flux.

17. The method of claim 16, wherein the shear is inversely proportional to a grating period and directly proportional to a grating order.

18. The method of claim 15, further comprising combining the first and second portions with at least one focusing optical element of focal length f, wherein the spatial frequency is inversely proportional to f.

19. An imaging polarimeter, comprising:
a first polarizing grating configured to diffract portions of an input light flux having a first state of polarization and a second state of polarization in a first direction and a second direction, respectively;
a second polarizing grating configured to receive the diffracted portions from the first polarizing grating and diffract the portions associated with the first state of polarization and the second state of polarization along the second direction and the first direction, respectively, so that the first and second portions propagate displaced from and parallel to each other;
a polarization analyzer configured to produce a common state of polarization of the first and second portions;
a focusing element configured to combine the first and second portions; and
a detector configured to receive the intensity pattern and produce a detected intensity pattern.

20. The polarimeter of claim 19, further comprising an image processor configured to produce a polarization image based on the detected intensity pattern.

21. The polarimeter of claim 20, wherein the detected intensity pattern is associated with a shear produced by the displacement of the first and second portions.

* * * * *